(12) United States Patent
Thomas et al.

(10) Patent No.: US 8,968,284 B2
(45) Date of Patent: Mar. 3, 2015

(54) APPARATUS AND METHODS FOR TREATING FEMALE URINARY INCONTINENCE

(71) Applicant: Verathon, Inc., Bothell, WA (US)

(72) Inventors: Simon W. H. Thomas, Danville, CA (US); Peter S. Edelstein, Menlo Park, CA (US); John T. To, Newark, CA (US); Benjamin T. Nordell, San Mateo, CA (US); Stuart D. Edwards, Corral de Tierra, CA (US)

(73) Assignee: Verathon Inc., Bothell, WA (US)

( * ) Notice: Subject to any disclaimer, the term of this patent is extended or adjusted under 35 U.S.C. 154(b) by 0 days.

(21) Appl. No.: 13/917,930

(22) Filed: Jun. 14, 2013

(65) Prior Publication Data

US 2013/0282006 A1 Oct. 24, 2013

Related U.S. Application Data

(63) Continuation of application No. 13/443,713, filed on Apr. 10, 2012, now Pat. No. 8,465,482, which is a continuation of application No. 11/431,213, filed on May 10, 2006, now Pat. No. 8,177,781, which is a (Continued)

(51) Int. Cl.
*A61B 18/18* (2006.01)
*A61B 18/00* (2006.01)
(Continued)

(52) U.S. Cl.
CPC ............ *A61B 18/00* (2013.01); *A61B 17/0625* (2013.01); *A61B 18/02* (2013.01);
(Continued)

(58) Field of Classification Search
USPC ...................................... 606/27–52
See application file for complete search history.

(56) References Cited

U.S. PATENT DOCUMENTS 373,399 A 11/1887 Hamilton
728,883 A 5/1903 Downes
(Continued)

FOREIGN PATENT DOCUMENTS

DE 3838840 5/1990
DE 4303882 8/1994
(Continued)

OTHER PUBLICATIONS

Castell et al.; Gastroesophageal Reflux Disease: Current Strategies for Patient Management; Arch Fam Med; Apr. 1996; 5(4); pp. 221-227.
(Continued)

*Primary Examiner* — Linda Dvorak
*Assistant Examiner* — Amanda Scott
(74) *Attorney, Agent, or Firm* — Shay Glenn LLP

(57) ABSTRACT

Apparatus and methods are provided for treating female urinary incontinence by applying a form of energy to tissue in the vicinity of the urethra and/or bladder outlet to change tissue compliance without substantially narrowing the urethral and/or bladder outlet lumen. The apparatus comprises an elongated shaft having a means for treating urethral tissue and an expandable member deployable distal of the means for treating. The expandable member is configured to be anchored against the bladder outlet to dispose the means for treating at a desired treatment site in the urethra using only tactile feedback. The means for treating may include a needleless RF electrode, an ultrasound transducer, or a cryogenic probe configured to be advanced through a hollow needle, each of which are designed to reduce or eliminate symptoms associated with urinary incontinence.

13 Claims, 12 Drawing Sheets

Related U.S. Application Data continuation of application No. 10/273,900, filed on Oct. 16, 2002, now Pat. No. 7,306,591, which is a continuation-in-part of application No. 10/207,689, filed on Jul. 25, 2002, now Pat. No. 7,291,129, which is a continuation-in-part of application No. 09/678,500, filed on Oct. 2, 2000, now Pat. No. 6,470,219.

(51) Int. Cl.
*A61B 17/062* (2006.01)
*A61B 18/02* (2006.01)
*A61B 18/14* (2006.01)
*A61N 1/06* (2006.01)
*A61B 17/00* (2006.01)
*A61N 7/02* (2006.01)

(52) U.S. Cl.
CPC ......... *A61B18/1477* (2013.01); *A61B 18/1485* (2013.01); *A61N 1/06* (2013.01); *A61B 18/14* (2013.01); *A61B 2017/00805* (2013.01); *A61B 2017/00867* (2013.01); *A61B 2018/00029* (2013.01); *A61B 2018/00035* (2013.01); *A61B 2018/00178* (2013.01); *A61B 2018/00285* (2013.01); *A61B 2018/00523* (2013.01); *A61B 2018/00553* (2013.01); *A61B 2018/00559* (2013.01); *A61B 2018/00916* (2013.01); *A61B 2018/1425* (2013.01); *A61B 2018/143* (2013.01); *A61B 2218/007* (2013.01); *A61N 7/022* (2013.01); *C08L 2201/12* (2013.01)
USPC .............................................. 606/27; 606/41

(56) References Cited

U.S. PATENT DOCUMENTS

| | | |
|---|---|---|
| 1,798,902 A | 3/1931 | Raney |
| 3,011,684 A | 12/1961 | Corneil |
| 3,353,491 A | 11/1967 | Bastian |
| 3,517,128 A | 6/1970 | Hines |
| 3,575,158 A | 4/1971 | Summers |
| 3,597,124 A | 8/1971 | Adams |
| 3,749,098 A | 7/1973 | De Bennetot |
| 3,901,241 A | 8/1975 | Allen, Jr. |
| 3,924,631 A | 12/1975 | Mancusi |
| 3,926,175 A | 12/1975 | Allen et al. |
| 3,939,821 A | 2/1976 | Roth |
| 4,011,872 A | 3/1977 | Komiya |
| 4,138,205 A | 2/1979 | Wallach |
| 4,187,057 A | 2/1980 | Xanthopoulos |
| 4,196,724 A | 4/1980 | Wirt et al. |
| 4,311,145 A | 1/1982 | Esty et al. |
| 4,311,154 A | 1/1982 | Sterzer et al. |
| 4,378,801 A | 4/1983 | Oosten |
| 4,381,007 A | 4/1983 | Doss |
| 4,409,453 A | 10/1983 | Smith |
| 4,411,266 A | 10/1983 | Cosman |
| 4,423,812 A | 1/1984 | Sato |
| 4,453,536 A | 6/1984 | Abild |
| 4,532,924 A | 8/1985 | Auth et al. |
| 4,552,516 A | 11/1985 | Stanley |
| 4,565,200 A | 1/1986 | Cosman |
| 4,568,255 A | 2/1986 | Lavender et al. |
| 4,587,975 A | 5/1986 | Salo et al. |
| 4,673,393 A | 6/1987 | Suzuki et al. |
| 4,674,506 A | 6/1987 | Alcond |
| 4,679,561 A | 7/1987 | Doss |
| 4,686,962 A | 8/1987 | Haber |
| 4,705,041 A | 11/1987 | Kim |
| 4,708,604 A | 11/1987 | Kidera |
| 4,742,829 A | 5/1988 | Law et al. |
| 4,765,331 A | 8/1988 | Petruzzi et al. |
| 4,773,393 A | 9/1988 | Haber et al. |
| 4,776,344 A | 10/1988 | Shirasaki et al. |
| 4,802,479 A | 2/1989 | Haber et al. |
| 4,807,620 A | 2/1989 | Strul et al. |
| 4,813,855 A | 3/1989 | Leveen et al. |
| 4,832,680 A | 5/1989 | Haber et al. |
| 4,832,688 A | 5/1989 | Sagae et al. |
| 4,838,506 A | 6/1989 | Cooper |
| 4,846,818 A | 7/1989 | Keldahl et al. |
| 4,878,492 A | 11/1989 | Sinofsky et al. |
| 4,901,737 A | 2/1990 | Toone |
| 4,906,203 A | 3/1990 | Margrave et al. |
| 4,907,589 A | 3/1990 | Cosman |
| 4,925,376 A | 5/1990 | Kahler |
| 4,943,290 A | 7/1990 | Rexroth et al. |
| 4,946,443 A | 8/1990 | Hauser et al. |
| 4,947,842 A | 8/1990 | Marchosky et al. |
| 4,955,377 A | 9/1990 | Lennox et al. |
| 4,966,597 A | 10/1990 | Cosman |
| 4,976,709 A | 12/1990 | Sand |
| 4,976,711 A | 12/1990 | Parins et al. |
| 4,994,019 A | 2/1991 | Fernandez et al. |
| 4,994,033 A | 2/1991 | Shockey et al. |
| 4,994,069 A | 2/1991 | Ritchart et al. |
| 5,002,558 A | 3/1991 | Klein et al. |
| 5,003,991 A | 4/1991 | Takayama et al. |
| 5,007,897 A | 4/1991 | Kalb et al. |
| 5,012,822 A | 5/1991 | Schwarz |
| 5,019,075 A | 5/1991 | Spears et al. |
| 5,035,696 A | 7/1991 | Rydell |
| 5,041,109 A | 8/1991 | Abela |
| 5,045,078 A | 9/1991 | Asta |
| 5,046,512 A | 9/1991 | Murchie |
| 5,047,028 A | 9/1991 | Qian |
| 5,049,132 A | 9/1991 | Shaffer et al. |
| 5,057,106 A | 10/1991 | Kasevich et al. |
| 5,083,565 A | 1/1992 | Parins |
| 5,084,044 A | 1/1992 | Quint |
| 5,088,522 A | 2/1992 | Rath et al. |
| 5,088,979 A | 2/1992 | Filipi et al. |
| 5,090,424 A | 2/1992 | Simon et al. |
| 5,092,841 A | 3/1992 | Spears |
| 5,094,233 A | 3/1992 | Brennan |
| 5,098,429 A | 3/1992 | Sterzer |
| 5,100,423 A | 3/1992 | Fearnot |
| 5,100,429 A | 3/1992 | Sinofsky et al. |
| 5,102,390 A | 4/1992 | Crittenden et al. |
| 5,103,804 A | 4/1992 | Abele et al. |
| 5,106,360 A | 4/1992 | Ishiwara et al. |
| 5,110,270 A | 5/1992 | Morrick |
| 5,122,137 A | 6/1992 | Lennox |
| 5,140,999 A | 8/1992 | Ardito |
| 5,151,909 A | 9/1992 | Davenport et al. |
| 5,156,151 A | 10/1992 | Imran |
| 5,188,596 A | 2/1993 | Condon et al. |
| 5,190,517 A | 3/1993 | Zieve et al. |
| 5,190,540 A | 3/1993 | Lee |
| 5,190,541 A | 3/1993 | Abele et al. |
| 5,197,963 A | 3/1993 | Parins |
| 5,197,964 A | 3/1993 | Parins |
| 5,199,951 A | 4/1993 | Spears |
| 5,201,732 A | 4/1993 | Parins et al. |
| 5,205,287 A | 4/1993 | Erbel et al. |
| 5,209,776 A | 5/1993 | Bass et al. |
| 5,213,580 A | 5/1993 | Slepian et al. |
| 5,215,103 A | 6/1993 | Desai |
| 5,215,450 A | 6/1993 | Tamari |
| 5,219,335 A | 6/1993 | Willard et al. |
| 5,219,355 A | 6/1993 | Parodi et al. |
| 5,232,444 A | 8/1993 | Just et al. |
| 5,234,409 A | 8/1993 | Goldberg et al. |
| 5,236,413 A | 8/1993 | Feiring |
| 5,239,982 A | 8/1993 | Trauthen |
| 5,239,999 A | 8/1993 | Imran |
| 5,242,441 A | 9/1993 | Avitall |
| 5,243,615 A | 9/1993 | Ortiz et al. |
| 5,254,126 A | 10/1993 | Filipi et al. |
| 5,256,133 A | 10/1993 | Spitz |
| 5,256,138 A | 10/1993 | Burek et al. |
| 5,257,451 A | 11/1993 | Edwards et al. |
| 5,263,493 A | 11/1993 | Avitall |

(56) References Cited

U.S. PATENT DOCUMENTS

| | | |
|---|---|---|
| 5,273,535 A | 12/1993 | Edwards et al. |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,278,201 A | 1/1994 | Dunn et al. |
| 5,281,216 A | 1/1994 | Klicek |
| 5,281,217 A | 1/1994 | Edwards et al. |
| 5,281,218 A | 1/1994 | Imran |
| 5,282,799 A | 2/1994 | Rydell |
| 5,286,254 A | 2/1994 | Shapland et al. |
| 5,292,321 A | 3/1994 | Lee |
| 5,293,869 A | 3/1994 | Edwards et al. |
| 5,300,099 A | 4/1994 | Rudie et al. |
| 5,304,123 A | 4/1994 | Atala et al. |
| 5,304,214 A | 4/1994 | DeFord et al. |
| 5,309,910 A | 5/1994 | Edwards et al. |
| 5,313,943 A | 5/1994 | Houser et al. |
| 5,314,465 A | 5/1994 | Maurer et al. |
| 5,314,466 A | 5/1994 | Stern et al. |
| 5,316,020 A | 5/1994 | Truffer |
| 5,318,531 A | 6/1994 | Leone |
| 5,322,503 A | 6/1994 | Desai |
| 5,324,284 A | 6/1994 | Imran |
| 5,324,288 A | 6/1994 | Billings et al. |
| 5,328,467 A | 7/1994 | Edwards et al. |
| 5,328,471 A | 7/1994 | Slepian |
| 5,330,518 A | 7/1994 | Neilson et al. |
| 5,334,196 A | 8/1994 | Scott et al. |
| 5,334,201 A | 8/1994 | Cowan |
| 5,336,222 A | 8/1994 | Durgin, Jr. et al. |
| 5,340,290 A | 8/1994 | Clemens |
| 5,342,181 A | 8/1994 | Schock et al. |
| 5,342,357 A | 8/1994 | Nardella |
| 5,344,435 A | 9/1994 | Turner et al. |
| 5,345,936 A | 9/1994 | Pomeranz et al. |
| 5,348,554 A | 9/1994 | Imran et al. |
| 5,349,825 A | 9/1994 | Duke et al. |
| 5,354,279 A | 10/1994 | Hofling |
| 5,363,861 A | 11/1994 | Edwards et al. |
| 5,365,926 A | 11/1994 | Desai |
| 5,365,945 A | 11/1994 | Halstrom |
| 5,368,557 A | 11/1994 | Nita et al. |
| 5,368,592 A | 11/1994 | Stern et al. |
| 5,370,671 A | 12/1994 | Maurer et al. |
| 5,370,675 A | 12/1994 | Edwards et al. |
| 5,370,677 A | 12/1994 | Rudie et al. |
| 5,370,678 A | 12/1994 | Edwards et al. |
| 5,374,261 A | 12/1994 | Yoon |
| 5,376,064 A | 12/1994 | Cerny |
| 5,383,876 A | 1/1995 | Nardella |
| 5,383,917 A | 1/1995 | Desai et al. |
| 5,385,544 A | 1/1995 | Edwards et al. |
| 5,388,972 A | 2/1995 | Calhoun et al. |
| 5,398,683 A | 3/1995 | Edwards et al. |
| 5,400,783 A | 3/1995 | Pomeranz et al. |
| 5,401,272 A | 3/1995 | Perkins |
| 5,403,311 A | 4/1995 | Abele et al. |
| 5,403,312 A | 4/1995 | Yates et al. |
| 5,405,322 A | 4/1995 | Lennox et al. |
| 5,405,346 A | 4/1995 | Grundy et al. |
| 5,405,369 A | 4/1995 | Selman et al. |
| 5,409,000 A | 4/1995 | Imran |
| 5,409,453 A | 4/1995 | Lundquist et al. |
| 5,409,483 A | 4/1995 | Campbell et al. |
| 5,411,475 A | 5/1995 | Atala et al. |
| 5,413,588 A | 5/1995 | Rudie et al. |
| 5,415,657 A | 5/1995 | Taymor-Luria |
| 5,417,208 A | 5/1995 | Winkler |
| 5,421,819 A | 6/1995 | Edwards et al. |
| 5,423,744 A | 6/1995 | Gencheff et al. |
| 5,423,808 A | 6/1995 | Edwards et al. |
| 5,423,812 A | 6/1995 | Ellman et al. |
| 5,428,486 A | 6/1995 | Nagase |
| 5,431,648 A | 7/1995 | Lev |
| 5,431,649 A | 7/1995 | Mulier et al. |
| 5,433,720 A | 7/1995 | Faccioli et al. |
| 5,433,739 A | 7/1995 | Sluijter et al. |
| 5,435,805 A | 7/1995 | Edwards et al. |
| 5,437,603 A | 8/1995 | Cerny et al. |
| 5,437,664 A | 8/1995 | Cohen et al. |
| 5,441,499 A | 8/1995 | Fritzsch |
| 5,443,470 A | 8/1995 | Stern et al. |
| 5,447,417 A | 9/1995 | Kuhl et al. |
| 5,447,529 A | 9/1995 | Marchlinski et al. |
| 5,448,990 A | 9/1995 | De Faria-Correa |
| 5,454,782 A | 10/1995 | Perkins |
| 5,454,807 A | 10/1995 | Lennox et al. |
| 5,454,809 A | 10/1995 | Janssen |
| 5,456,662 A | 10/1995 | Edwards et al. |
| 5,456,682 A | 10/1995 | Edwards et al. |
| 5,458,568 A | 10/1995 | Racchini et al. |
| 5,458,596 A | 10/1995 | Lax et al. |
| 5,458,597 A | 10/1995 | Edwards et al. |
| 5,462,545 A | 10/1995 | Wang et al. |
| 5,464,395 A | 11/1995 | Faxon et al. |
| 5,464,404 A | 11/1995 | Abela et al. |
| 5,465,717 A | 11/1995 | Imran et al. |
| 5,470,308 A | 11/1995 | Edwards et al. |
| 5,470,309 A | 11/1995 | Edwards et al. |
| 5,471,982 A | 12/1995 | Edwards et al. |
| 5,472,441 A | 12/1995 | Edwards et al. |
| 5,480,417 A | 1/1996 | Hascoet et al. |
| 5,484,400 A | 1/1996 | Edwards et al. |
| 5,485,849 A | 1/1996 | Panescu et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,496,312 A | 3/1996 | Klicek |
| 5,498,238 A | 3/1996 | Shapland et al. |
| 5,499,971 A | 3/1996 | Shapland et al. |
| 5,500,012 A | 3/1996 | Brucker et al. |
| 5,505,730 A | 4/1996 | Edwards |
| 5,507,743 A | 4/1996 | Edwards et al. |
| 5,509,929 A | 4/1996 | Hascoet et al. |
| 5,514,130 A | 5/1996 | Baker |
| 5,514,131 A | 5/1996 | Edwards et al. |
| 5,514,669 A | 5/1996 | Selman |
| 5,516,396 A | 5/1996 | Maurer et al. |
| 5,520,684 A | 5/1996 | Imran |
| 5,531,676 A | 7/1996 | Edwards et al. |
| 5,533,999 A | 7/1996 | Hood et al. |
| 5,536,267 A | 7/1996 | Edwards et al. |
| 5,540,655 A | 7/1996 | Edwards et al. |
| 5,540,679 A | 7/1996 | Fram et al. |
| 5,542,915 A | 8/1996 | Edwards et al. |
| 5,542,916 A | 8/1996 | Hirsch et al. |
| 5,545,161 A | 8/1996 | Imran |
| 5,545,171 A | 8/1996 | Sharkey et al. |
| 5,545,193 A | 8/1996 | Fleischman et al. |
| 5,545,434 A | 8/1996 | Huarng |
| 5,549,108 A | 8/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,556,396 A | 9/1996 | Cohen et al. |
| 5,558,672 A | 9/1996 | Edwards et al. |
| 5,558,673 A | 9/1996 | Edwards et al. |
| 5,562,720 A | 10/1996 | Stern et al. |
| 5,569,241 A | 10/1996 | Edwards |
| 5,571,116 A | 11/1996 | Bolanos et al. |
| 5,575,788 A | 11/1996 | Baker et al. |
| 5,588,432 A | 12/1996 | Crowley |
| 5,588,960 A | 12/1996 | Edwards et al. |
| 5,588,961 A | 12/1996 | Leone et al. |
| 5,591,199 A | 1/1997 | Porter et al. |
| 5,595,183 A | 1/1997 | Swanson et al. |
| 5,599,294 A | 2/1997 | Edwards et al. |
| 5,599,307 A | 2/1997 | Bacher et al. |
| 5,599,345 A | 2/1997 | Edwards et al. |
| 5,599,346 A | 2/1997 | Edwards et al. |
| 5,601,591 A | 2/1997 | Edwards et al. |
| 5,607,422 A | 3/1997 | Smeets et al. |

(56) References Cited

U.S. PATENT DOCUMENTS

| | | |
|---|---|---|
| 5,609,151 A | 3/1997 | Mulier et al. |
| 5,609,598 A | 3/1997 | Laufer et al. |
| 5,624,439 A | 4/1997 | Edwards et al. |
| 5,628,770 A | 5/1997 | Thome et al. |
| 5,630,794 A | 5/1997 | Lax et al. |
| 5,630,812 A * | 5/1997 | Ellman et al. .................. 606/41 |
| 5,634,899 A | 6/1997 | Shapland et al. |
| 5,647,868 A | 7/1997 | Chinn |
| 5,649,973 A | 7/1997 | Tierney et al. |
| 5,660,836 A | 8/1997 | Knowlton |
| 5,666,954 A | 9/1997 | Chapelon et al. |
| 5,667,488 A | 9/1997 | Lundquist et al. |
| 5,672,153 A | 9/1997 | Lax et al. |
| 5,673,695 A | 10/1997 | McGee et al. |
| 5,674,191 A | 10/1997 | Edwards et al. |
| 5,674,287 A | 10/1997 | Slepian et al. |
| 5,681,308 A | 10/1997 | Edwards et al. |
| 5,683,384 A | 11/1997 | Gough et al. |
| 5,685,839 A | 11/1997 | Edwards et al. |
| 5,687,723 A | 11/1997 | Avitall |
| 5,688,266 A | 11/1997 | Edwards et al. |
| 5,688,267 A | 11/1997 | Panescu et al. |
| 5,688,490 A | 11/1997 | Tournier et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,702,438 A | 12/1997 | Avitall |
| 5,704,908 A | 1/1998 | Hofmann et al. |
| 5,707,349 A | 1/1998 | Edwards |
| 5,709,224 A | 1/1998 | Behl et al. |
| 5,709,539 A | 1/1998 | Hammer et al. |
| 5,709,653 A | 1/1998 | Leone |
| 5,715,817 A | 2/1998 | Stevens-Wright et al. |
| 5,718,702 A | 2/1998 | Edwards |
| 5,720,718 A | 2/1998 | Rosen et al. |
| 5,720,719 A | 2/1998 | Edwards et al. |
| 5,728,066 A | 3/1998 | Daneshvar |
| 5,728,094 A | 3/1998 | Edwards |
| 5,728,144 A | 3/1998 | Edwards et al. |
| 5,730,719 A | 3/1998 | Edwards |
| 5,732,698 A | 3/1998 | Swanson et al. |
| 5,733,319 A | 3/1998 | Neilson et al. |
| 5,738,096 A | 4/1998 | Ben-Haim |
| 5,738,114 A | 4/1998 | Edwards |
| 5,741,225 A | 4/1998 | Lax et al. |
| 5,743,870 A | 4/1998 | Edwards |
| 5,743,904 A | 4/1998 | Edwards |
| 5,746,224 A | 5/1998 | Edwards |
| 5,752,813 A | 5/1998 | Tyner et al. |
| 5,755,753 A | 5/1998 | Knowlton |
| 5,766,234 A | 6/1998 | Chen et al. |
| 5,769,846 A | 6/1998 | Edwards et al. |
| 5,769,879 A | 6/1998 | Richards et al. |
| 5,769,880 A | 6/1998 | Truckai et al. |
| 5,772,255 A | 6/1998 | Osborne et al. |
| 5,779,673 A | 7/1998 | Roth et al. |
| 5,785,642 A | 7/1998 | Wallace et al. |
| 5,795,288 A | 8/1998 | Cohen et al. |
| 5,797,903 A | 8/1998 | Swanson et al. |
| 5,800,482 A | 9/1998 | Pomeranz et al. |
| 5,800,484 A | 9/1998 | Gough et al. |
| 5,807,333 A | 9/1998 | Osborne et al. |
| 5,807,395 A | 9/1998 | Mulier et al. |
| 5,810,763 A | 9/1998 | Feiring |
| 5,813,411 A | 9/1998 | Van Bladel et al. |
| 5,823,197 A | 10/1998 | Edwards |
| 5,827,273 A | 10/1998 | Edwards |
| 5,830,213 A | 11/1998 | Panescu et al. |
| 5,836,314 A | 11/1998 | Benderev et al. |
| 5,836,874 A | 11/1998 | Swanson et al. |
| 5,840,076 A | 11/1998 | Swanson et al. |
| 5,843,016 A | 12/1998 | Lugnani et al. |
| 5,843,077 A | 12/1998 | Edwards |
| 5,843,156 A | 12/1998 | Slepian et al. |
| 5,846,218 A | 12/1998 | Brisken et al. |
| 5,846,238 A | 12/1998 | Jackson et al. |
| 5,860,974 A | 1/1999 | Abele |
| 5,865,801 A | 2/1999 | Houser |
| 5,868,708 A | 2/1999 | Hart et al. |
| 5,871,469 A | 2/1999 | Eggers et al. |
| 5,871,483 A | 2/1999 | Jackson et al. |
| 5,873,877 A | 2/1999 | McGaffigan et al. |
| 5,879,348 A | 3/1999 | Owens et al. |
| 5,882,346 A | 3/1999 | Pomeranz et al. |
| 5,891,135 A | 4/1999 | Jackson et al. |
| 5,895,417 A | 4/1999 | Pomeranz et al. |
| 5,916,235 A | 6/1999 | Guglielmi |
| 5,921,954 A | 7/1999 | Mohr, Jr. et al. |
| 5,921,982 A | 7/1999 | Lesh et al. |
| 5,938,660 A | 8/1999 | Swartz et al. |
| 5,957,920 A * | 9/1999 | Baker ............................ 606/33 |
| 5,961,513 A | 10/1999 | Swanson et al. |
| 5,964,755 A | 10/1999 | Edwards |
| 5,964,782 A | 10/1999 | LaFontaine et al. |
| 5,964,791 A | 10/1999 | Bolmsjo |
| 5,968,041 A | 10/1999 | Edwards |
| 5,971,983 A | 10/1999 | Lesh |
| 5,989,284 A | 11/1999 | Laufer |
| 5,995,875 A | 11/1999 | Blewett et al. |
| 6,002,968 A | 12/1999 | Edwards |
| 6,006,755 A | 12/1999 | Edwards |
| 6,009,877 A | 1/2000 | Edwards |
| 6,013,053 A | 1/2000 | Bower et al. |
| 6,015,406 A | 1/2000 | Goble et al. |
| 6,015,407 A | 1/2000 | Rieb et al. |
| 6,016,437 A | 1/2000 | Tu et al. |
| 6,027,499 A | 2/2000 | Johnston et al. |
| 6,035,238 A | 3/2000 | Ingle et al. |
| 6,036,689 A | 3/2000 | Tu et al. |
| 6,044,846 A | 4/2000 | Edwards |
| 6,044,847 A | 4/2000 | Carter et al. |
| 6,045,496 A | 4/2000 | Pacella et al. |
| 6,047,700 A | 4/2000 | Eggers et al. |
| 6,048,329 A | 4/2000 | Thompson et al. |
| 6,056,744 A | 5/2000 | Edwards |
| 6,056,747 A | 5/2000 | Saadat et al. |
| 6,063,045 A | 5/2000 | Wax et al. |
| 6,068,628 A | 5/2000 | Fanton et al. |
| 6,071,230 A | 6/2000 | Henalla |
| 6,071,279 A | 6/2000 | Whayne et al. |
| 6,073,052 A | 6/2000 | Zelickson et al. |
| 6,077,257 A | 6/2000 | Edwards et al. |
| 6,081,749 A | 6/2000 | Ingle et al. |
| 6,091,995 A | 7/2000 | Ingle et al. |
| 6,092,528 A | 7/2000 | Edwards |
| 6,096,052 A | 8/2000 | Callister et al. |
| 6,099,526 A | 8/2000 | Whayne et al. |
| 6,104,959 A | 8/2000 | Spertell |
| 6,106,521 A | 8/2000 | Blewett et al. |
| 6,136,010 A | 10/2000 | Modesitt et al. |
| 6,139,569 A | 10/2000 | Ingle et al. |
| 6,142,993 A | 11/2000 | Whayne et al. |
| 6,156,032 A | 12/2000 | Lennox |
| 6,156,060 A | 12/2000 | Roy et al. |
| 6,159,170 A | 12/2000 | Borodulin et al. |
| 6,159,236 A | 12/2000 | Biel |
| 6,162,217 A | 12/2000 | Kannenberg et al. |
| 6,164,921 A | 12/2000 | Moubayed et al. |
| 6,165,172 A | 12/2000 | Farley et al. |
| 6,168,594 B1 | 1/2001 | Lafontaine et al. |
| 6,179,824 B1 | 1/2001 | Eggers et al. |
| 6,179,831 B1 | 1/2001 | Bliweis |
| 6,190,382 B1 | 2/2001 | Ormsby et al. |
| 6,200,333 B1 | 3/2001 | Laufer |
| 6,216,027 B1 | 4/2001 | Willis et al. |
| 6,216,704 B1 | 4/2001 | Ingle et al. |
| 6,231,514 B1 | 5/2001 | Lowe et al. |
| 6,231,570 B1 | 5/2001 | Tu et al. |
| 6,231,591 B1 | 5/2001 | Desai |
| 6,236,891 B1 | 5/2001 | Ingle et al. |
| 6,241,753 B1 | 6/2001 | Knowlton |
| 6,254,586 B1 | 7/2001 | Mann et al. |
| 6,254,598 B1 | 7/2001 | Edwards et al. |

(56) References Cited

U.S. PATENT DOCUMENTS

| | | | |
|---|---|---|---|
| 6,254,599 B1 | 7/2001 | Lesh et al. |
| 6,258,087 B1 | 7/2001 | Edwards et al. |
| 6,273,886 B1 | 8/2001 | Edwards et al. |
| 6,283,987 B1 | 9/2001 | Laird et al. |
| 6,283,989 B1 | 9/2001 | Laufer et al. |
| 6,292,700 B1 * | 9/2001 | Morrison et al. ............... 607/98 |
| 6,322,584 B2 | 11/2001 | Ingle et al. |
| 6,325,798 B1 | 12/2001 | Edwards et al. |
| 6,338,726 B1 | 1/2002 | Edwards et al. |
| 6,355,031 B1 | 3/2002 | Edwards et al. |
| 6,358,245 B1 | 3/2002 | Edwards et al. |
| 6,394,998 B1 | 5/2002 | Wallace et al. |
| 6,402,744 B2 | 6/2002 | Edwards et al. |
| 6,409,723 B1 | 6/2002 | Edwards |
| 6,413,253 B1 | 7/2002 | Koop et al. |
| 6,416,504 B2 | 7/2002 | Mosel et al. |
| 6,423,058 B1 | 7/2002 | Edwards et al. |
| 6,425,853 B1 | 7/2002 | Edwards |
| 6,425,854 B1 | 7/2002 | Galt et al. |
| 6,425,877 B1 | 7/2002 | Edwards |
| 6,428,538 B1 | 8/2002 | Blewett et al. |
| 6,432,116 B1 | 8/2002 | Callister et al. |
| 6,440,127 B2 * | 8/2002 | McGovern et al. ............ 606/41 |
| 6,440,128 B1 | 8/2002 | Edwards et al. |
| 6,447,505 B2 * | 9/2002 | McGovern et al. ............ 606/41 |
| 6,460,542 B1 | 10/2002 | James |
| 6,463,331 B1 * | 10/2002 | Edwards ..................... 607/101 |
| 6,464,689 B1 | 10/2002 | Qin et al. |
| 6,464,697 B1 | 10/2002 | Edwards et al. |
| 6,470,219 B1 | 10/2002 | Edwards et al. |
| 6,478,775 B1 | 11/2002 | Galt et al. |
| 6,480,746 B1 | 11/2002 | Ingle et al. |
| 6,500,175 B1 | 12/2002 | Gough et al. |
| 6,506,189 B1 | 1/2003 | Rittman, III et al. |
| 6,511,475 B1 | 1/2003 | Altshuler et al. |
| 6,517,534 B1 * | 2/2003 | McGovern et al. ............ 606/41 |
| 6,544,226 B1 | 4/2003 | Gaiser et al. |
| 6,544,260 B1 | 4/2003 | Markel et al. |
| 6,547,776 B1 | 4/2003 | Gaiser et al. |
| 6,554,824 B2 | 4/2003 | Davenport et al. |
| 6,554,825 B1 | 4/2003 | Murray et al. |
| 6,561,998 B1 | 5/2003 | Roth et al. |
| 6,579,266 B2 | 6/2003 | Mosel et al. |
| 6,589,238 B2 | 7/2003 | Edwards et al. |
| 6,607,525 B2 | 8/2003 | Franco |
| 6,613,047 B2 | 9/2003 | Edwards |
| 6,645,201 B1 | 11/2003 | Utley et al. |
| 6,666,848 B2 | 12/2003 | Stone |
| 6,685,623 B2 | 2/2004 | Presthus et al. |
| 6,692,490 B1 | 2/2004 | Edwards |
| 6,699,243 B2 | 3/2004 | West et al. |
| 6,712,810 B2 | 3/2004 | Harrington et al. |
| 6,733,495 B1 | 5/2004 | Bek et al. |
| 6,743,165 B2 | 6/2004 | Mosel et al. |
| 6,743,197 B1 | 6/2004 | Edwards |
| 6,743,226 B2 * | 6/2004 | Cosman et al. ................. 606/41 |
| 6,749,607 B2 | 6/2004 | Edwards et al. |
| 6,783,523 B2 | 8/2004 | Qin et al. |
| 6,790,207 B2 | 9/2004 | Utley et al. |
| 6,802,841 B2 | 10/2004 | Utley et al. |
| 6,821,276 B2 * | 11/2004 | Lambrecht et al. ............ 606/45 |
| 6,827,713 B2 | 12/2004 | Bek et al. |
| 6,830,052 B2 | 12/2004 | Carter et al. |
| 6,836,688 B2 | 12/2004 | Ingle et al. |
| 6,840,954 B2 | 1/2005 | Dietz et al. |
| 6,843,789 B2 | 1/2005 | Goble |
| 6,852,110 B2 | 2/2005 | Roy et al. |
| 6,866,663 B2 | 3/2005 | Edwards et al. |
| 6,882,885 B2 | 4/2005 | Levy, Jr. et al. |
| 6,893,435 B2 | 5/2005 | Goble |
| 6,953,461 B2 | 10/2005 | McClurken et al. |
| 6,976,492 B2 * | 12/2005 | Ingle et al. ................... 128/898 |
| 6,986,764 B2 | 1/2006 | Davenport et al. |
| 6,994,704 B2 | 2/2006 | Qin et al. |
| 7,008,419 B2 | 3/2006 | Shadduck |
| 7,022,105 B1 | 4/2006 | Edwards |
| 7,052,453 B2 | 5/2006 | Presthus et al. |
| 7,073,504 B2 | 7/2006 | Callister et al. |
| 7,077,841 B2 | 7/2006 | Gaiser et al. |
| 7,160,270 B2 | 1/2007 | West et al. |
| 7,165,551 B2 | 1/2007 | Edwards et al. |
| 7,179,219 B2 | 2/2007 | Matlock |
| 7,184,827 B1 | 2/2007 | Edwards |
| 7,291,129 B2 | 11/2007 | Li et al. |
| 7,306,591 B2 | 12/2007 | Thomas et al. |
| 7,317,949 B2 | 1/2008 | Morrison et al. |
| 7,326,207 B2 | 2/2008 | Edwards |
| 7,326,235 B2 | 2/2008 | Edwards |
| 7,329,254 B2 | 2/2008 | West et al. |
| 7,422,587 B2 | 9/2008 | Bek et al. |
| 7,462,179 B2 | 12/2008 | Edwards et al. |
| 7,468,060 B2 | 12/2008 | Utley et al. |
| 7,615,049 B2 | 11/2009 | West et al. |
| 7,648,500 B2 | 1/2010 | Edwards et al. |
| 7,722,338 B2 | 5/2010 | Nordell et al. |
| 8,177,781 B2 | 5/2012 | Thomas et al. |
| 8,353,908 B2 | 1/2013 | Edwards et al. |
| 8,412,318 B2 | 4/2013 | Edwards et al. |
| 8,465,482 B2 | 6/2013 | Thomas et al. |
| 2001/0018597 A1 | 8/2001 | Gellman et al. |
| 2002/0156531 A1 | 10/2002 | Felt et al. |
| 2002/0161380 A1 | 10/2002 | Saitou et al. |
| 2003/0130710 A1 | 7/2003 | Baker et al. |
| 2003/0191513 A1 | 10/2003 | Manker et al. |
| 2004/0044340 A1 | 3/2004 | Francischelli et al. |
| 2004/0087995 A1 | 5/2004 | Copa et al. |
| 2004/0097901 A1 | 5/2004 | Whalen et al. |
| 2005/0070938 A1 | 3/2005 | Copa et al. |
| 2005/0090815 A1 | 4/2005 | Francischelli et al. |
| 2005/0131431 A1 | 6/2005 | Copa et al. |
| 2006/0155261 A1 | 7/2006 | Bek et al. |
| 2006/0205996 A1 | 9/2006 | Presthus et al. |
| 2006/0224157 A1 | 10/2006 | Utley et al. |
| 2007/0112340 A1 * | 5/2007 | Thomas et al. ................. 606/27 |
| 2009/0125018 A1 | 5/2009 | Merrick et al. |
| 2010/0049186 A1 | 2/2010 | Ingle et al. |
| 2010/0114087 A1 | 5/2010 | Edwards et al. |
| 2012/0136407 A1 | 5/2012 | Presthus |
| 2013/0197505 A1 | 8/2013 | Edwards et al. |

FOREIGN PATENT DOCUMENTS

| | | |
|---|---|---|
| EP | 0139607 A1 | 5/1985 |
| EP | 0608609 B1 | 9/2001 |
| GB | 2069063 A | 8/1981 |
| GB | 2269538 A | 2/1994 |
| JP | 02-121675 | 5/1990 |
| JP | 04-044739 | 2/1992 |
| JP | 04-246367 | 9/1992 |
| JP | 2000-342598 | 12/2000 |
| JP | 01-514921 A | 9/2001 |
| JP | 02-503512 A | 2/2002 |
| WO | WO 85/02779 A1 | 7/1985 |
| WO | WO 91/01773 A1 | 2/1991 |
| WO | WO 92/10142 A1 | 6/1992 |
| WO | WO 93/08755 A1 | 5/1993 |
| WO | WO 93/15664 A1 | 8/1993 |
| WO | WO 94/10925 A1 | 5/1994 |
| WO | WO 94/21165 A1 | 9/1994 |
| WO | WO 94/21178 A1 | 9/1994 |
| WO | WO 94/22366 A1 | 10/1994 |
| WO | WO 94/26178 A1 | 11/1994 |
| WO | WO 95/08289 A2 | 3/1995 |
| WO | WO 95/18575 A1 | 7/1995 |
| WO | WO 95/19142 A1 | 7/1995 |
| WO | WO 95/25472 A1 | 9/1995 |
| WO | WO 96/00042 A1 | 1/1996 |
| WO | WO 96/16606 A1 | 6/1996 |
| WO | WO 96/29946 A1 | 10/1996 |
| WO | WO 96/36288 A1 | 11/1996 |
| WO | WO 97/06857 A2 | 2/1997 |
| WO | WO 97/15238 A1 | 5/1997 |
| WO | WO 97/20191 A1 | 6/1997 |
| WO | WO 97/20510 A1 | 6/1997 |

(56) References Cited

FOREIGN PATENT DOCUMENTS

| WO | WO 97/23532 A1 | 7/1997 |
|---|---|---|
| WO | WO 97/24992 A1 | 7/1997 |
| WO | WO 97/32532 A1 | 9/1997 |
| WO | WO 97/39688 A2 | 10/1997 |
| WO | WO 97/43970 A1 | 11/1997 |
| WO | WO 97/43971 A2 | 11/1997 |
| WO | WO 98/01087 A1 | 1/1998 |
| WO | WO 98/05286 A1 | 2/1998 |
| WO | WO 98/05380 A1 | 2/1998 |
| WO | WO 98/38936 A1 | 9/1998 |
| WO | WO 99/08614 A1 | 2/1999 |
| WO | WO 99/16502 A1 | 4/1999 |
| WO | WO 99/35983 A1 | 7/1999 |
| WO | WO 99/44522 A1 | 9/1999 |
| WO | WO 00/62696 A1 | 10/2000 |
| WO | WO 00/66052 A1 | 11/2000 |
| WO | WO 01/06942 A1 | 2/2001 |
| WO | WO 01/22897 A1 | 4/2001 |
| WO | WO 01/34018 A2 | 5/2001 |
| WO | WO 02/28475 A1 | 4/2002 |
| WO | WO 02/091935 A1 | 11/2002 |

OTHER PUBLICATIONS

Dallemagne et al.; Laparoscopic Nissen Fundoplication: Preliminary Report; Surgical Laparoscopy & Endoscopy; Sep. 1991 1(3): 138-43.
Hinder et al.; The Technique of Laparosopic Nissen Fundoplication; Surgical Laparoscopy & Endoscopy; Sep. 1992. 2(3): 265-272.
Kaneko et al.; Physiological Laryngeal Pacemaker; Trans Am Soc Artif Intern Organs; May 1985; vol. XXXI; pp. 293-296.
Karlstrom et al; Ectopic jejunal pacemakers and enterogastric reflux after Roux gastrectomy: Effect of intestinal pacing; Surgery; Sep. 1989; 106(3); 486-495.
Kelly et al; Doudenal-gastric reflux and slowed gastric emptying by electrical pacing of the canine duodenal pacesetter potential; Gastroenterology; Mar. 1977; 72(3); 429-33.
Mugica et al.; Direct Diaphragm Stimulation; Jan. 1987; PACE; vol. 10; pp. 252-256.
Mugica et al.; Neurostimulation: An Overview, Chapter 21, Preliminary Test of a Muscular Diaphragm Pacing System on Human Patients; (year of publication is sufficiently earlier than the effective U.S. filing date and any foreign priority date) 1985; pp. 263-279.
Nochomovitz et al.; Electrical Activation of the Diaphragm; Clinics in Chest Medicine; Jun. 1988; vol. 9; No. 2; pp. 349-358.
Prior et al.; Treatment of Menorrhagia by Radiofrequency Heating; Int. J. Hyperthermia; Mar.-Apr. 1991; vol. 7; No. 2; pp. 213-220.
Reynolds, J. C.; Influence of pathophysiology, severity, and cost on the medical management of gastroesophageal reflux disease; Am J Health-Syst Pharm; Nov. 15, 1996; 53 (22 Suppl 3); S5-12.
Rice et al.; Endoscopic Paranasal Sinus Surgery, Chapter 5, Functional Endoscopic Paranasal Sinus Surgery; The Technique of Messerklinger; Raven Press; (year of publication is sufficiently earlier than the effective U.S. filing date and any foreign priority date) 1988; pp. 75-102.
Rice et al.; Endoscopic Paranasal Sinus Surgery, Chapter 6, Total Endoscopic Sphenoethmoidectomy; The Technique of Wigand; Raven Press; (year of publication is sufficiently earlier than the effective U.S. filing date and any foreign priority date) 1988; pp. 103-125.
Slepian; Polymeric Endoluminal Paving and Sealing; Textbook of Interventional Cardiology; WB Saunders Publishing; pp. 647-670; 1990 (year of publication is sufficiently earlier than the effective U.S. filing date and any foreign priority date).
Tissue; Electromagnetic Spectrum, The Visible Spectrum; Copyright 1996; updated Nov. 3, 1996. 1 page; retrieved online from: Science Hypermedia Home Page; http://www.scimedia.com/checm-ed/light/edm-spec.htm. (printed Mar. 30, 2011).
Urschel, J.D.; Complications of Antireflux Surgery; Am J Surg; Jul. 1993; 166(1); 68-70.
Edwards, Stuart; U.S. Appl. No. 12/698,841 entitled "Treatment of urinary incontinence and other disorders by application of energy and drugs," filed Feb. 2, 2010.
Hayes et al.; Prediction of transient temperature fields and cumulative tissue destruction for radio frequency heating of a tumor; Medical Physics (Am. Assoc. Phy. Med.); 12(6), 684-692 pages; Nov./Dec. 1985.
Ingle et al.; U.S. Appl. No. 12/432,488 entitled "Noninvasive devices, methods, and systems for modifying tissues," filed Apr. 29, 2009.

* cited by examiner

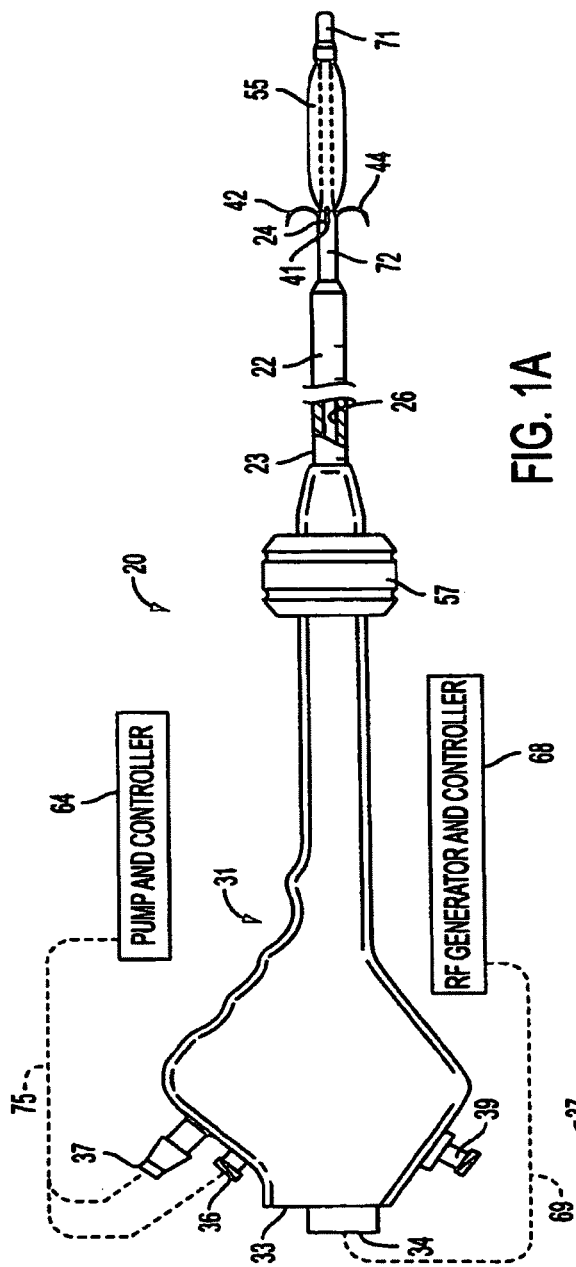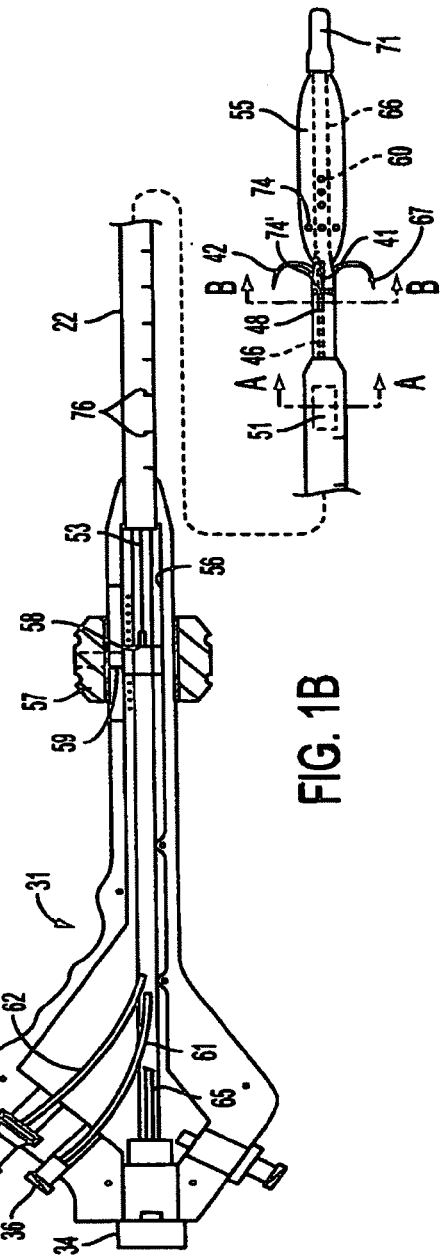

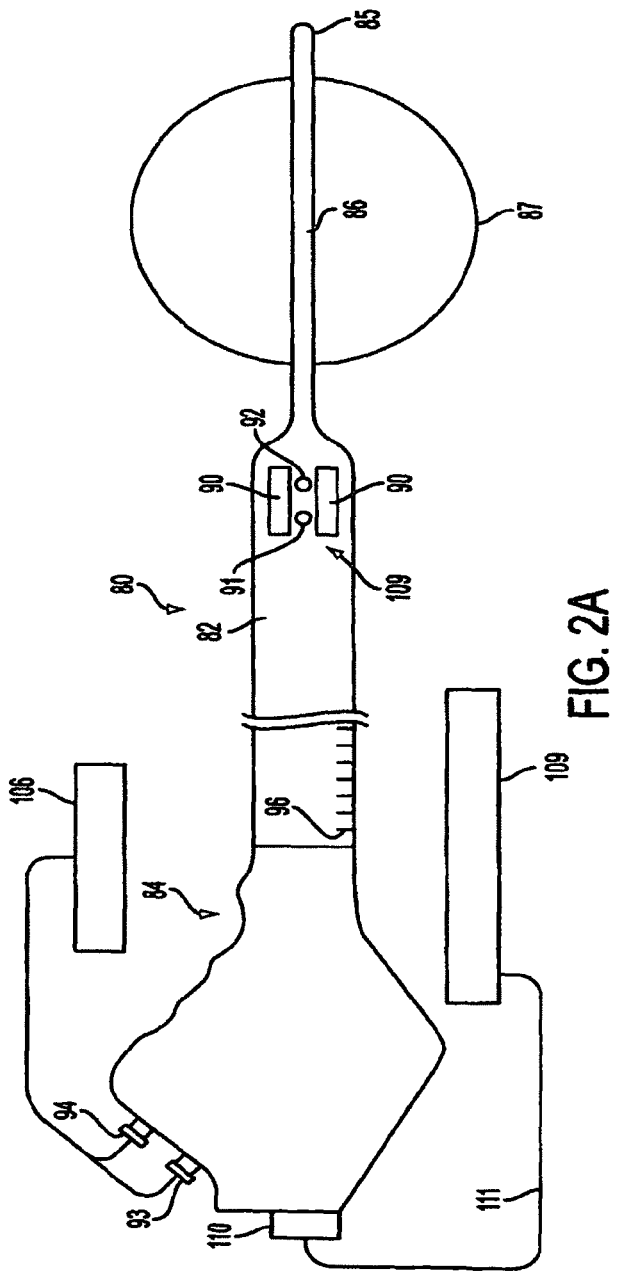
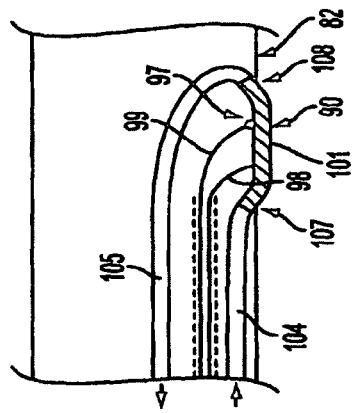
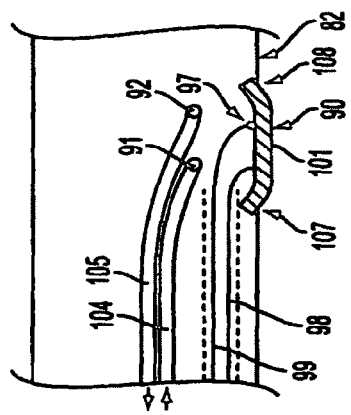

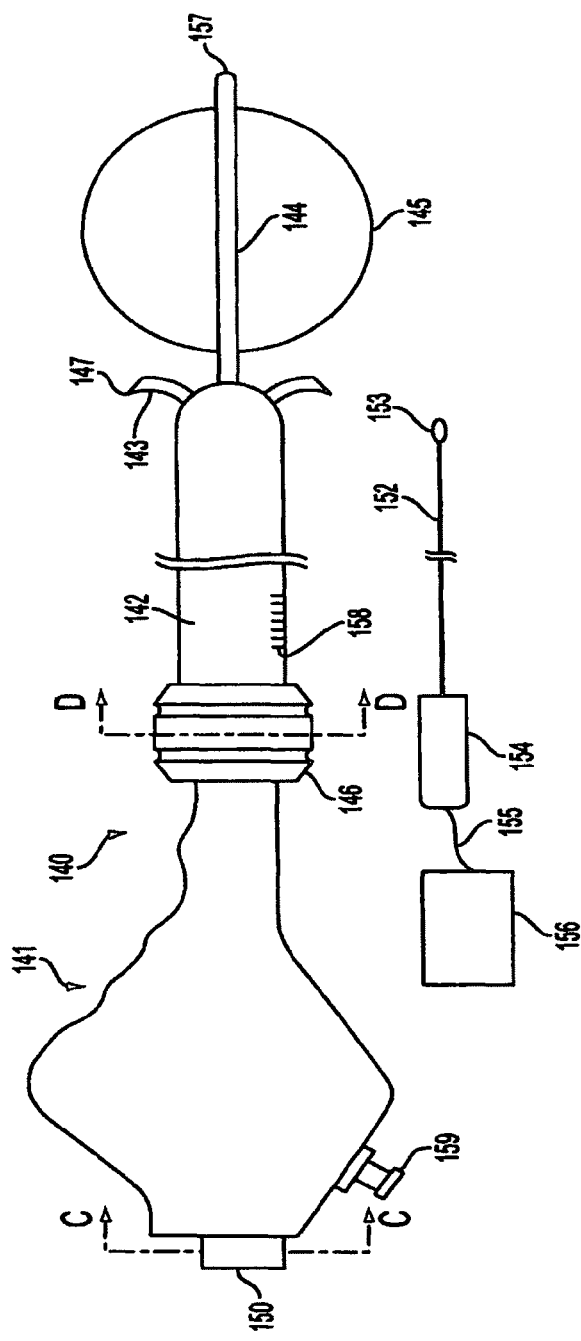
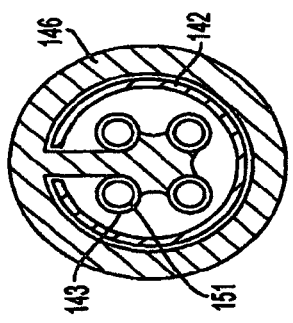
FIG. 6C
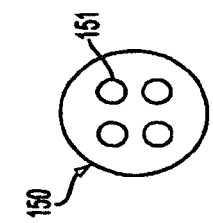
FIG. 6A
FIG. 6B

APPARATUS AND METHODS FOR TREATING FEMALE URINARY INCONTINENCE

CROSS REFERENCE TO RELATED APPLICATIONS

The present application is a continuation of U.S. patent application Ser. No. 13/443,713, filed Apr. 10, 2012, Publication No. US-2012-0197247-A1, which is a continuation of U.S. patent application Ser. No. 11/431,213, filed May 10, 2006, now U.S. Pat. No. 8,177,781, which is a continuation of U.S. patent application Ser. No. 10/273,900, filed Oct. 16, 2002, now U.S. Pat. No. 7,306,591, which is a continuation-in-part of U.S. patent application Ser. No. 10/207,689, filed Jul. 25, 2002, now U.S. Pat. No. 7,291,129, which is a continuation-in-part of U.S. patent application Ser. No. 09/678,500, filed Oct. 2, 2000, now U.S. Pat. No. 6,470,219, each of which is incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This invention relates to apparatus and methods for treating urinary incontinence, and more particularly, for treating female urinary incontinence in humans by applying a selected form of energy to tissue in the vicinity of the urethra and/or bladder outlet to cause a change in tissue compliance without substantially narrowing the urethral lumen and/or bladder outlet.

BACKGROUND

The term "urinary incontinence" refers to the involuntary leakage of urine from the body in an uncontrolled manner. One cause of incontinence is increased mobility of the bladder outlet (bladder outlet hypermobility) where the bladder and proximal urethra do not maintain their normal anatomic positions during transient periods of increased bladder pressure due to increased intra-abdominal pressure. In addition, there is a small region of circular muscle surrounding the middle portion of the urethra in the female called the "urethral sphincter," which also participates in the controlled release of urine from the bladder. If the bladder outlet becomes too mobile and/or if the urinary sphincter or any other part of the urinary system malfunctions, the result may be urinary incontinence.

Urinary incontinence can generally be characterized into two types, one of which is called "stress incontinence" and the other "urge incontinence." Stress incontinence refers to involuntary loss of urine during coughing, laughing, sneezing, jogging or other physical activity that causes a sufficient increase in intra-abdominal pressure. Urge incontinence refers to the involuntary loss of urine due to unwanted bladder contraction that may be associated with an uncontrollable desire to urinate. "Mixed incontinence" refers to a combination of both urge and stress incontinence.

Heretofore, many different types of treatment have been utilized to treat female urinary incontinence including surgical and non-surgical procedures including the injection, under cystoscopic and/or fluoroscopic visualization, of collagen or other material into the tissue surrounding or adjacent to the bladder outlet and/or proximal urethra. In addition, drug therapy also has been utilized, for example, drugs to treat the detrusor muscle, which is the bladder wall muscle responsible for contracting and emptying the bladder. All of these procedures and therapies have drawbacks, are relatively expensive, and in the case of injections, require the equipment and training necessary to perform cystoscopic and/or fluoroscopic visualization of the urethra and bladder outlet. There is therefore a need for a new and improved apparatus and method for treatment of female urinary incontinence.

In view of the drawbacks of previously-known devices, it would be desirable to provide apparatus and methods for treating female urinary incontinence using an elongated shaft configured to be introduced via the urethral orifice and advanced through the urethral lumen to enable energy delivery to surrounding tissue.

It further would be desirable to provide apparatus and methods for treating female urinary incontinence that allow a physician to remodel the urethral wall and/or bladder outlet without the need for a visualization device, e.g., a cystoscope or fluoroscope.

It still further would be desirable to provide apparatus and methods for treating female urinary incontinence by techniques that do not carry risks associated with surgical incisions, such as infection and herniation, and do not result in external scarring.

SUMMARY OF THE DISCLOSURE

In view of the foregoing, it is an object of the present invention to provide apparatus and methods for treating female urinary incontinence using an elongated shaft configured to be introduced via the urethral orifice and advanced through the urethral lumen to enable energy delivery to surrounding tissue.

It further is an object of the present invention to provide apparatus and methods for treating female urinary incontinence that allow a physician to remodel the urethral wall and/or bladder outlet without the need for a visualization device, e.g., a cystoscope or fluoroscope.

It still further is an object of the present invention to provide apparatus and methods for treating female urinary incontinence by techniques that do not carry risks associated with surgical incisions, such as infection and herniation, and do not result in external scarring or require dressings or bandages.

These and other objects of the present invention are accomplished by providing apparatus comprising a handle, an elongated shaft having a distal region, an expandable member, and means for treating the submucosal layer of the urethral wall and/or bladder outlet to cause a change in tissue compliance without substantially narrowing the urethral and/or bladder outlet lumen.

In a preferred embodiment, the handle is coupled to a proximal end of the elongated shaft and is manipulated by the physician to insert the distal region into a patient's urethra, either individually or using an appropriate introducer sheath. The handle includes an actuator for deploying the expandable member.

In accordance with one aspect of the present invention, the expandable member is deployable at a predetermined distance distal of the means for treating. The expandable member may comprise a balloon or mechanically actuated basket that is configured to be moved between a contracted position, which permits insertion of the expandable member through the urethra and into the patient's bladder, and a deployed position, wherein the expandable member anchors against the bladder outlet. The expandable member facilitates tactile alignment of the means for treating at a desired treatment site, without the need for direct visualization.

In one embodiment of the present invention, the means for treating comprises at least one needleless electrode embedded in a lateral surface of the elongated shaft. The needleless electrode is coupled to a radio frequency generator/controller that causes the electrode to reach a desired temperature to heat the urethral tissue. In accordance with principles of the present invention, cooling fluid is provided in the vicinity of the electrode to cool the urethral and bladder outlet mucosa during the provision of RF energy. The application of RF energy causes denaturation of collagen in small localized areas where treatment is delivered. Following cessation of energy delivery, these microscopic foci of denatured collagen renature and heal, ultimately creating minute areas of decreased tissue compliance without substantial anatomic change.

In an alternative embodiments of the present invention, the means for treating comprises an ultrasound transducer disposed on the elongated shaft. The ultrasound transducer is coupled to an ultrasound generator/controller. Ultrasound beams generated by the transducer may be focused in accordance with known techniques to cause a rise in tissue temperature at a desired distance beneath the mucosal layer of the urethra. Collagen denaturation and subsequent renaturation caused by the rise in temperature changes the tissue compliance in the vicinity of the urethra and/or bladder outlet without substantial anatomic change.

In a further alternative embodiment of the present invention, the means for treating comprises at least one hollow needle having contracted and deployed states and a cryogenic probe adapted to be inserted through the hollow needle. In the contracted state, the hollow needle is disposed within the confines of the elongated shaft, while in the deployed state, the hollow needle extends beyond the elongated shaft to pierce through urethral tissue and/or bladder outlet mucosa. The cryogenic probe is advanced through the hollow needle to a treatment site within the urethral tissue to locally freeze tissue and cause necrosis, which in turn causes remodeling of tissue in the vicinity of the urethra and/or bladder outlet.

Methods of using the apparatus of the present invention to induce localized areas of decreased tissue compliance, and to reduce or eliminate the effects of urinary incontinence, also are provided.

BRIEF DESCRIPTION OF THE DRAWINGS

Further features of the invention, its nature and various advantages will be more apparent from the accompanying drawings and the following detailed description of the preferred embodiments, in which:

FIGS. 1A-1E are, respectively, side and side sectional views of a device to treat urinary incontinence, cross-sectional views along lines A-A and B-B of FIG. 1B, and a schematic view depicting use of apparatus of FIG. 1A;

FIGS. 2A-2C are, respectively, a side view of a first embodiment of the present invention and side sectional views of alternative means for cooling the mucosa in conjunction with the apparatus of FIG. 2A;

FIGS. 6A-6C are, respectively, a side view of a further alternative embodiment of the present invention, and cross-sectional views along lines C-C and D-D of FIG. 6A;

DETAILED DESCRIPTION

Figure 1C:
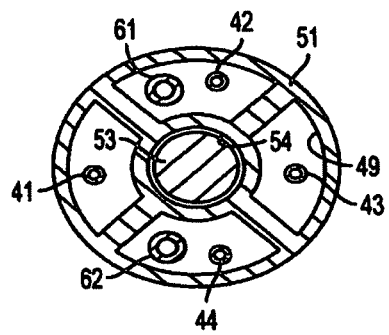

Referring now to FIG. 1, a device to treat urinary incontinence, described in U.S. Pat. No. 6,470,219, which is herein incorporated by reference in its entirety, is shown. Apparatus 20 comprises semi-rigid elongated tubular shaft 22 having proximal and distal extremities 23 and 24, distal region 72, and lumen 26 extending from proximal extremity 23 to distal extremity 24.

Handle 31 has proximal and distal ends, and is configured to be grasped by the human hand. The distal end of handle 31 is coupled to proximal extremity 23 of elongated shaft 22. The proximal end of handle 31 preferably comprises rear surface 33 through which electrical connector 34 extends. Handle 31 further comprises fluid-in port 36, fluid-out port 37 and, optionally, auxiliary port 39.

It will be apparent to those skilled in the art that handle 31 may comprise any suitable exterior shape that is configured to be grasped by a human hand, and is not intended to be limited by the exterior shapes depicted herein. An illustrative, alternative handle shape is depicted in commonly-assigned U.S. patent application Ser. No. 10/207,689, which is herein incorporated by reference in its entirety.

Figure 1D:
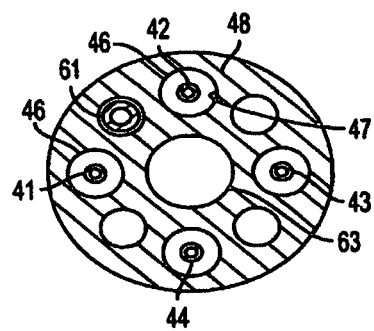

Plurality of needle electrodes 41-44, which are sharpened at their distal extremities, are disposed within distal region 72 of elongated shaft 22 in a contracted state. Needle electrodes 41-44 assume a preformed shape in a deployed state, i.e., when they are no longer constrained within elongated shaft 22, and preferably comprise a shape-memory material such as a nickel-titanium alloy. In the deployed state, needle electrodes 41-44 curve outwardly and downwardly to provide a fishhook-like configuration, as shown in FIG. 1A. Needle electrodes 41-44 are disposed in suitable angular positions, as for example, spaced circumferentially in a single plane 90° apart. This is accomplished by slidably mounting needle electrodes 41-44 in plurality of PEEK hypotubes 46 in four spaced-apart lumens 47 of Pebax block 48, as shown in FIG. 1D.

Pebax block 48 is mounted in a fixed position in distal region 72 of elongated shaft 22. Needle electrodes 41-44 extend proximally through hypotubes 46 and are mounted in fixed positions in four lumens 49 spaced apart in Pebax block 51, as shown in FIG. 1C.

Pebax block 51 is slidably mounted within elongated shaft 22. Rod 53 has a distal extremity mounted in a fixed position in centrally disposed lumen 54 of block 51 and extends proximally from block 51 and into recess 56 of handle 31. Slide block 58 has outwardly extending protrusion 59 coupled to rod 53, as shown in FIG. 1B. Knob 57 is slidably mounted on the exterior of handle 31 and is secured to protrusion 59, e.g., using a screw. Movement of knob 57 longitudinally with respect to handle 31 causes needle electrodes 41-44 to be moved between extended and retracted positions in hypotubes 46.

Cooling liquid preferably is supplied via elongated shaft 22 so that it is discharged in the vicinity of needle electrodes 41-44 via tubing 61. Tubing 61 is in turn connected to fitting 36. Tubing 62 is connected to fitting 37 and extends distally into lumen 26 of tubular member 22, through block 51, and terminates at block 48, where it is placed in communication with return lumen 63 in block 48. Tubing 61 continues through block 48 and opens into shaft 66, which extends distally from block 48.

Expandable member 55 is disposed on shaft 66 and illustratively comprises a balloon. As will be described hereinbelow with respect to FIGS. 8A-8B, expandable member 55 alternatively may comprise a mechanically self-deployable basket.

Shaft 66 has openings 60 disposed within expandable member 55. Openings 60 are in fluid communication with tubing 61 and are used to inflate expandable member 55. Expandable member 55 is provided with plurality of openings 74 through which the cooling liquid introduced into expandable member 55 may escape and be discharged in the vicinity of needle electrodes 41-44 to cool the tissue being treated, as hereinafter described. The cooling liquid, after it has performed its function, is aspirated through central return lumen 63 to fitting 37. Alternatively, openings 74 may be disposed directly in a lateral surface of shaft 22, as depicted by openings 74' in FIG. 1B.

Fittings 36 and 37 are connected by tubing 75 to irrigation pump/controller 64, as depicted in FIG. 1A. Controller 64 supplies a cooling liquid, such as room temperature water, to fitting 36 and may also aspirate the liquid through fitting 37 after it has been used.

Plurality of insulated wires 65 are connected to electrical connector 34 with slack being provided within handle 31. Electrical connector 34 is adapted to be connected to RF generator/controller 68 by cable 69, as depicted in FIG. 1A.

Wires 65 extend distally through lumen 26 of elongated shaft 22, through lumens in blocks 48 and 51, and are coupled to four thermocouple wires (not shown) extending through hollow needles 41-44. The thermocouple wires are connected to thermocouples 67, which are mounted in sharpened tips of needles 41-44 for measuring needle-tip temperatures, as shown in FIG. 1B.

Figure 1E:
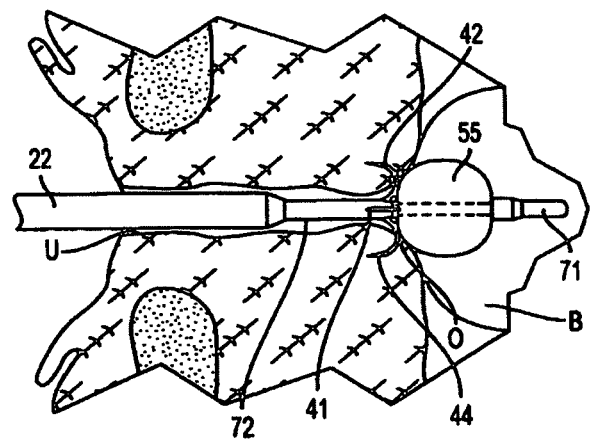

Referring now to FIG. 1E, a preferred method for treating urinary incontinence using apparatus 20 is described. Atraumatic tip 71, which is disposed distal of expandable member 55, is inserted into urethra U of a patient with expandable member 55 and needles 41-44 being provided in contracted states. Elongated shaft 22 is distally advanced within urethra U so that expandable member 55 is positioned within bladder B, e.g., using markings 76 of FIG. 1B. Expandable member 55 then is deployed, e.g., by inflating a balloon via fluid-in port 36. Expandable member 55 then is retracted proximally so that expandable member 55 is anchored against bladder outlet O, as shown in FIG. 1E.

After expandable member 55 has been seated against bladder outlet O, a physician distally advances knob 57 with respect to handle 31 to cause needles 41-44 to be advanced from their retracted positions within distal region 72 of elongated shaft 22. Needles 41-44 move distally and sidewise beyond the outer cylindrical profile of elongated shaft 22 and into the urethral tissue in the vicinity of bladder outlet O, as shown in FIG. 1E.

After needles 41-44 have been deployed, radio frequency energy is supplied from RF generator/controller 68. As is well known to those skilled in the art, such a generator may be configured to provide impedance readings that give an indication of whether or not needle electrodes 41-44 have been properly positioned within the tissue.

Liquid is introduced in the vicinity of needle electrodes 41-44 via irrigation pump/controller 64 and openings 74, as described hereinabove, to cool the mucosal layer of the urethral wall. Radio frequency energy then is supplied to the needle electrodes at a power level ranging from 1 to 10 watts for a period of time ranging from 60 to 90 seconds to achieve approximately an 70° C. temperature in the tissue being treated, while the overlying mucosal tissue is preserved by the cooling liquid flow. In accordance with one aspect of the present invention, it is desirable that the tissue not to reach a temperature of 100° C. Therefore, RF generator 68, utilizing the information supplied from thermocouples 67, is programmed to automatically turn off if the temperature reaches a pre-set temperature, e.g., 80° C. Otherwise, for the duration of the treatment, the RF power is adjusted to maintain the tissue being treated at the desired target temperature.

Once the first RF treatment has been completed, the radio frequency energy is turned off and knob 57 is retracted to withdraw needle electrodes 41-44 into their retracted positions within distal region 72 of elongated shaft 22. The device then may be rotated a predetermined angle, the needles redeployed and another radio frequency energy treatment may be applied to surrounding tissue. During this entire procedure, irrigation liquid is introduced through openings 74 of expandable member 55 and/or openings 74' of shaft 22. As the irrigation fluid progressively fills the bladder during each RF treatment, the geometry of the bladder outlet changes as the bladder is filled such that repeated seating of the expandable member results in the electrode location moving progressively towards the bladder outlet.

In connection with the RF treatments described hereinabove, tiny sites of collagen in the vicinity of the treatment site renature over the ensuing weeks. Such treatment results in changes in tissue compliance of the bladder outlet and/or urethral walls to cause a significant improvement in urinary incontinence.

Figure 3:
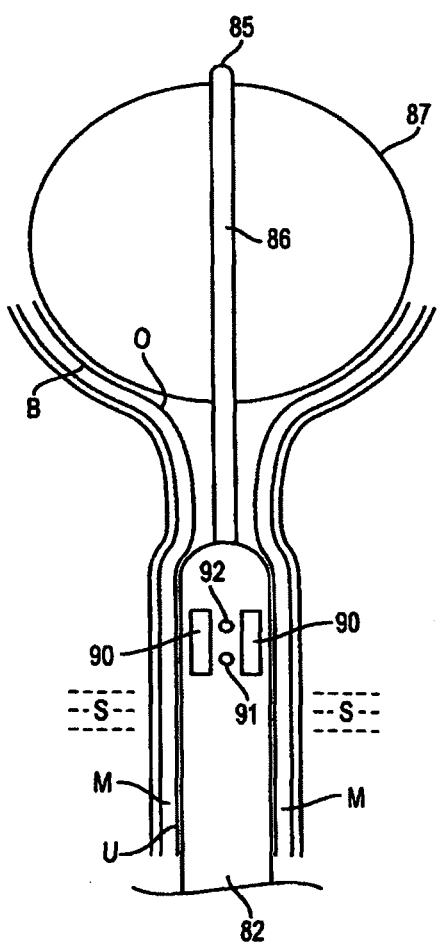
FIG. 3 is a schematic view depicting the use of apparatus of FIG. 2.

Referring now to FIGS. 2-3, a first embodiment of the present invention that utilizes a plurality of needleless electrodes to treat urinary incontinence is described. Apparatus 80 comprises elongated shaft 82 having proximal and distal ends and distal region 86 disposed adjacent to the distal end. Handle 84 is provided in accordance with handle 31 of FIG. 1, except as noted below, and is coupled to the proximal end of elongated shaft 82.

Elongated shaft 82 further comprises at least one needleless electrode 90 capable of transmitting radio frequency energy. Needleless electrode 90 may comprise a hollow, curved surface, as depicted in FIGS. 2B-2C, and preferably is manufactured from stainless steel. Needleless electrode 90 preferably is embedded into a lateral surface of elongated shaft 82 so that curved regions 107 and 108 of electrode 90 extend within an interior portion of elongated shaft 82, while outer surface 101 of electrode 90 is disposed outside of and faces away from elongated shaft 82, as shown in FIGS. 2B-2C.

Elongated shaft 82 further comprises irrigation port 91 and optional aspiration port 92, which are coupled to irrigation tubing 104 and aspiration tubing 105, respectively. Irrigation tubing 104 and aspiration tubing 105 extend proximally from their respective ports 91 and 92, through elongated shaft 82 and handle 84, and are coupled to fluid-in and fluid-out ports 93 and 94, respectively. Fluid-in and fluid-out ports 93 and 94 in turn are coupled to fluid controller 106.

In FIGS. 2A and 2B, irrigation and aspiration ports 91 and 92 are illustratively disposed in a lateral surface of elongated shaft 82 adjacent to electrode 90. In an alternative embodiment shown in FIG. 2C, irrigation and aspiration ports 91 and 92 may be omitted and irrigation and aspiration tubing 104 and 105 may be coupled to first and second curved ends 107 and 108 of hollow electrode 90, respectively. In this embodiment, fluid infused into irrigation tubing 104 flows through hollow electrode 90 to provide a cooling effect upon outer surface 101, then is aspirated through tubing 105.

Apparatus 80 of FIG. 2 further comprises wire 98 and thermocouple wire 99, each having proximal and distal ends. The distal ends of wire 98 and thermocouple wire 99 are coupled to needleless electrode 90, as shown in FIGS. 2B-2C, while the proximal ends extend through elongated shaft 82 and handle 84. Wire 98 and thermocouple wire 99 preferably are coupled to electrical connector 110 of handle 84, which in turn is connected to RF generator/controller 109 by cable 111.

Apparatus 80 further comprises expandable member 87 that is deployable at a predetermined distance distal of needleless electrode 90. Expandable member 87 may comprise a balloon that is disposed on distal region 86 or, alternatively, a self-expanding mechanical basket as described hereinbelow with respect to FIGS. 8A-8B.

Referring now to FIG. 3, a preferred method for using apparatus 80 of FIG. 2A is described. In a first step, atraumatic tip 85 at the distal end of elongated shaft 82 is inserted into a patient's urethra U with expandable member 87 in a contracted state. Expandable member 87 is positioned within bladder B, e.g., using measurement indicia 96 disposed near the proximal end of elongated shaft 82 (see FIG. 2A). Expandable member 87 is deployed and handle 84 is retracted proximally so that expandable member 87 is anchored against bladder outlet O.

In accordance with the present invention, retracting expandable member 87 against bladder outlet O positions needleless electrodes 90 at a desired treatment site within urethra U using only tactile feedback. Once properly positioned, liquid is introduced to irrigation port 91 via irrigation pump 106 to provide a cooling effect to mucosal layer M of the urethra. Radio frequency energy then is supplied to needleless electrode 90 to achieve a temperature of approximately 70° C. in the tissue being treated, i.e., the submucosal tissue S of the urethral wall. The overlying mucosal tissue M is preserved by the cooling liquid flow. Preferably, the submucosal tissue is not heated to a temperature significantly higher than 70° C. Therefore, RF generator 109, utilizing the information supplied from thermocouple 97, preferably is programmed to automatically turn off if the temperature reaches a pre-set temperature, as for example, 80° C. Otherwise, for the duration of the treatment, the RF power is adjusted to maintain the sub-mucosal tissue at the desired target temperature.

After this first RF treatment has been completed, the radio frequency energy is turned off and the device can be advanced into the bladder lumen and rotated a predetermined angle so that needleless electrode 90 may contact a new interior surface of urethra U. Once electrode 90 has been rotated to the desired angle, handle 84 is retracted proximally to seat expandable member 87 in bladder outlet O, and RF energy is provided to needleless electrode 90, as described hereinabove. Upon completion of the procedure, expandable member 87 is contracted and elongated shaft 82 is removed from the patient's urethra.

As described hereinabove with respect to the embodiment of FIGS. 1A-1E, the RF treatments produce collagen denaturation in small, localized areas where the treatment is delivered, followed by collagen renaturation and remodeling over the ensuing weeks and months, thereby resulting in changes in tissue compliance within the urethra and/or bladder outlet.

Figure 4:
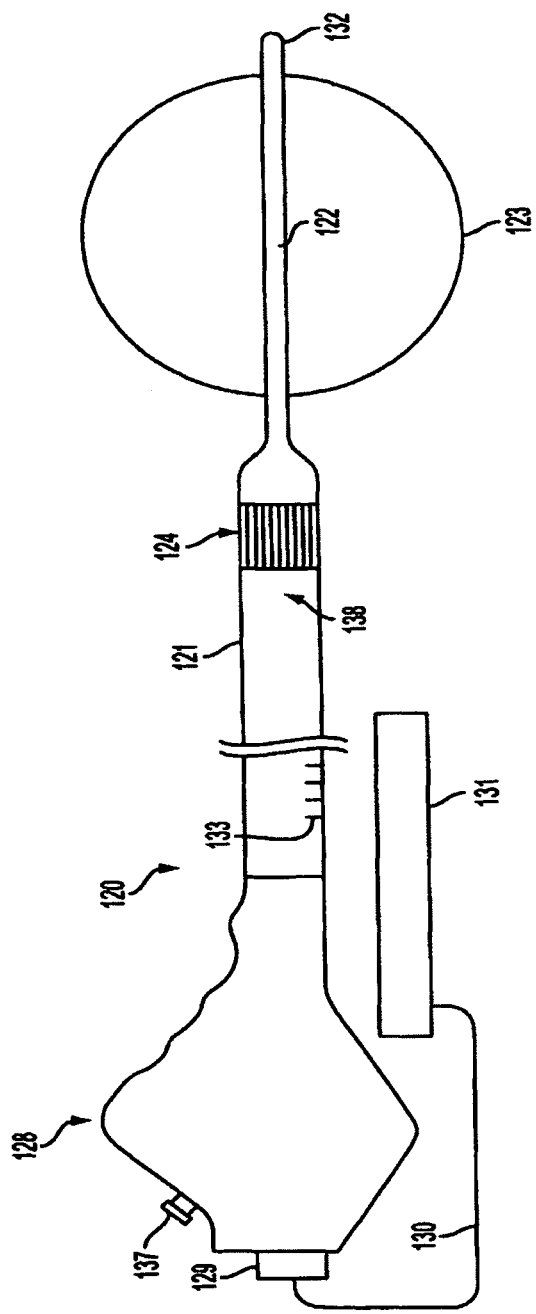
FIG. 4 is a side view of an alternative embodiment of the present invention.
Figure 5:
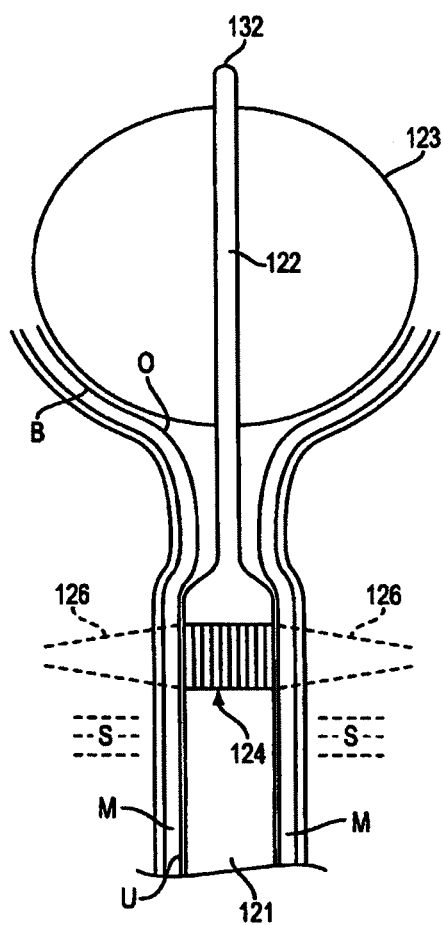
FIG. 5 is a schematic view depicting the use of apparatus of FIG. 4.

Referring now to FIGS. 4-5, a further alternative embodiment of the present invention is described wherein high intensity focused ultrasound (HIFU) is applied to treat urinary incontinence. HIFU involves directing high intensity ultrasound waves at the selected tissue to create heat in a precise area and cause coagulation and tissue necrosis.

In FIG. 4, apparatus 120 comprises elongated shaft 121 having proximal and distal ends and distal region 122 disposed adjacent to the distal end. Handle 128 is coupled to the proximal end of elongated shaft 121 and may comprise inflation port 137 that is in fluid communication with expandable member 123, illustratively a balloon. Alternatively, expandable member 123 may comprise a self-expanding mechanical basket as described hereinbelow with respect to FIGS. 8A-8B.

Elongated shaft 121 further comprises therapeutic ultrasound transducer 124 disposed on elongated shaft 121 just proximal of distal region 122. Ultrasound transducer 124 is capable of transmitting at therapeutic ultrasound frequencies. Transducer 124 preferably comprises an annular phased array, and is coupled to a transmission cable (not shown) disposed in a lumen of elongated shaft 121. The transmission cable extends proximally and is coupled to electrical connector 129 of handle 128. Electrical connector 129 in turn is connected to ultrasound generator/controller 131 by cable 130, as depicted in FIG. 4.

Referring now to FIG. 5, a preferred method of using apparatus 120 of FIG. 4 is described. Atraumatic tip 132 at the distal end of elongated shaft 121 is inserted into a patient's urethra U with expandable member 123 in a contracted state. Expandable member 123 is positioned within a patient's bladder B, e.g., using measurement indicia 133 of FIG. 4. Expandable member 123 then is deployed and handle 128 is retracted proximally so that expandable member 123 is anchored against bladder outlet O. In accordance with the present invention, retracting expandable member 123 against bladder outlet O positions transducer 124 at a desired treatment site within urethra U using only tactile feedback.

Ultrasound generator/controller 131 is turned on and set to the desired frequency to cause transducer 124 to emit ultrasonic beams. Ultrasound beams 126 are focused to cause a rise in tissue temperature at a desired distance beneath mucosal layer M of urethra U. The heating of the desired submucosal tissue causes localized denaturation of the tissue. The change in submucosal tissue created by the denaturation and renaturation of the collagen results in changes in tissue compliance of the urethral wall and/or bladder outlet, thereby reducing urinary incontinence.

Figure 7:
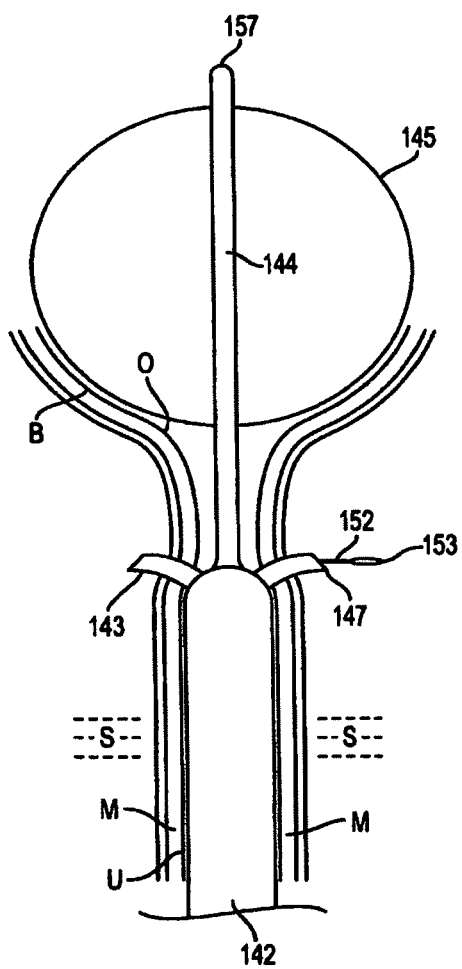
FIG. 7 is a schematic view depicting the use of apparatus of FIG. 6.

Referring now to FIGS. 6-7, a further alternative embodiment of the present invention is described whereby cryogenic therapy is used to treat urinary incontinence by controlled freezing of selected urethral tissue.

In FIG. 6A, cryogenic therapy apparatus 140 comprises elongated shaft 142 having proximal and distal ends and reduced diameter distal region 144 disposed adjacent to the distal end. Handle 141 is coupled to the proximal end of elongated shaft 142 and may comprise inflation port 159 that is in fluid communication with expandable member 145, illustratively a balloon. Alternatively, expandable member 145 may comprise a self-expanding mechanical basket as described hereinbelow with respect to FIGS. 8A-8B.

Apparatus 140 further comprises at least one hollow needle 143 and cryogenic probe 152. Needle 143 has proximal and distal ends and sharpened tip 147 disposed at the distal end. The proximal end of each hollow needle 143 is coupled to knob 146. Although four hollow needles are illustrated in FIG. 6C, it will be apparent to those skilled in the art that greater or fewer needles may be used.

Handle 141 further comprises proximal port 150 having at least one probe insertion hypotube 151, as depicted in FIG. 6B. Each probe insertion hypotube 151 corresponds to a respective needle 143. Each probe insertion hypotube 151 comprises an outer diameter that preferably is slightly smaller than an inner diameter of hollow needle 143. A proximal end of each probe insertion hypotube 151 is affixed to proximal port 150 while a distal end of each hypotube 151 extends into the proximal end of its respective hollow needle 143 to create an overlap between the distal end of the hypotube and the proximal end of the needle, as shown in FIG. 6C. This overlap allows needles 143 to move with respect to probe insertion hypotubes 151 when knob 146 is actuated.

Cryogenic probe 152 has proximal and distal ends and tip 153 disposed at the distal end. Handle 154 is coupled to the proximal end of cryogenic probe 152 and is configured to be grasped by a physician. Cryogenic probe 152 is powered and controlled by cryogenic generator 156 via wire 155, which is coupled to handle 154. Cryogenic probe 152 comprises an outer diameter configured to be inserted into probe insertion hypotube 151 and through hollow needle 143.

Referring now to FIG. 7, a preferred method of using apparatus 140 of FIG. 6A to treat urinary incontinence is described. Atraumatic tip 157 at the distal end of elongated shaft 142 is inserted into a patient's urethra U with needle 143 in a contracted state, i.e., retracted within the confines of elongated shaft 142, and also with expandable member 145 provided in a contracted state. Expandable member 145 is positioned within a patient's bladder B, e.g., using measurement indicia 158. Expandable member 157 then is deployed within bladder B and handle 141 is retracted proximally so that expandable member 157 is anchored against bladder outlet O. In accordance with one aspect of the present invention, retracting expandable member 157 against bladder outlet O positions needle 143, when deployed, at a desired treatment site within urethra U using only tactile feedback.

Needle 143 then is actuated by distally advancing knob 146, which urges needle 143 to extend beyond elongated shaft 142, pierce mucosal layer M of urethra U, and extend into submucosal layer S. Needle 143 preferably comprises a shape-memory material that causes the distal end to curve to a predetermined shape when needle 143 is no longer confined within elongated shaft 142.

Cryogenic probe 152 then is inserted into probe insertion hypotube 151 at proximal port 150 and is advanced distally via probe insertion hypotube 151 into hollow needle 143. Cryogenic probe 152 is advanced distally until it extends distal of needle 143 and into submucosal layer S of the urethra, as shown in FIG. 7. Needle 143, having a larger diameter relative to probe 152, serves to dilate the submucosal tissue prior to insertion of the probe so that the probe encounters reduced resistance from the tissue.

Cryogenic generator 156 is turned on and set to the desired temperature, which preferably is between about −80° F. and −110° F., to cause local regions of the submucosal tissue to freeze. The local regions of tissue and tip 153 may freeze together for about three minutes, after which time probe 152 is defrosted and removed from within elongated shaft 142 and handle 141. If desired, a physician then may re-insert probe 152 into a different insertion hypotube 151 and the procedure may be repeated through a different needle 143 to treat another region within submucosal layer S. In accordance with principles of the present invention, the application of cryogenic probe 152 to the submucosal tissue causes small localized regions of submucosal tissue to undergo necrosis, after which tissue healing ensues. This results in altered tissue elasticity, tensile strength, and tissue compliance in the urethra and/or bladder outlet, and causes a significant improvement in urinary incontinence.

Figure 8A:
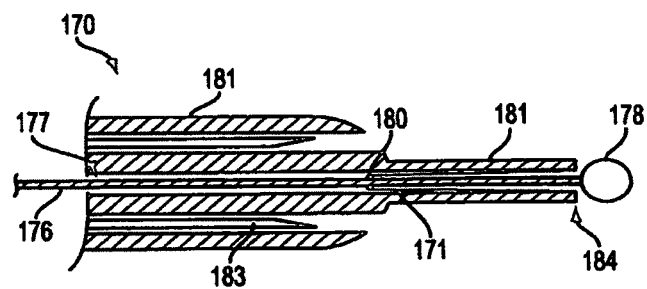
FIGS. 8A-8B are side sectional views illustrating the use of an alternative expandable member.
Figure 8B:
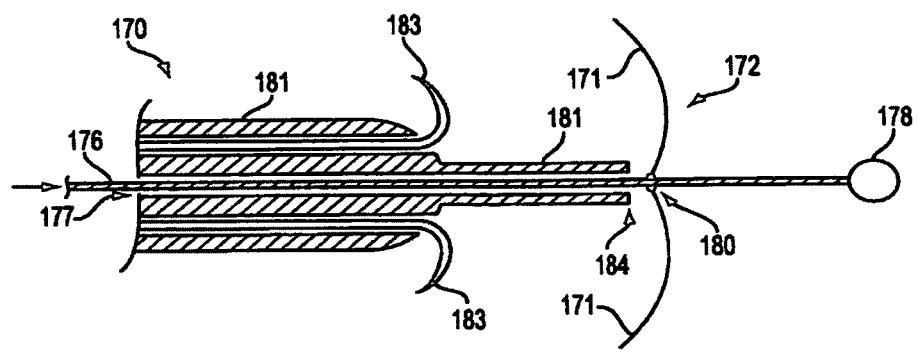

Referring now to FIGS. 8A-8B, an alternative expandable member is described for use with any of the treatment techniques described hereinabove. Apparatus 170 comprises self-expandable basket 172, shown in a deployed state in FIG. 8B, instead of a balloon. Basket 172 preferably comprises a plurality of flexible struts 171 joined to rod 176 via hinges 180. Struts 171, which may be covered by a biocompatible elastomeric membrane (not shown), are constrained in a contracted position within central lumen 177 of elongated shaft 181, as illustrated in FIG. 8A. Struts 171, which preferably comprise a shape-memory material such as Nitinol, assume a predetermined curvature extending radially outward from elongated shaft 181 in the deployed state, i.e., when struts 171 are no longer effectively constrained within central lumen 177, as shown in FIG. 8B.

Rod 176 has proximal and distal ends and is disposed through central lumen 177. Preferably, rod 176 includes atraumatic distal tip 178 disposed at the distal end. The proximal end of rod 176 is configured to be manipulated by a physician.

In operation, atraumatic tip 178 and elongated shaft 181 are inserted into the patient's urethra in a manner described hereinabove. Once distal end 184 of elongated shaft 181 is positioned within a patient's bladder, the proximal end of rod 176 is advanced distally by a physician to self-deploy mechanically expandable basket 172, as depicted in FIG. 8B. Once basket 172 is deployed within the bladder, elongated shaft 181 and rod 176 are retracted proximally to cause basket 172 to become anchored against the bladder outlet.

At this time, needles 183 may be deployed from elongated shaft 181 to penetrate the urethral wall to perform a radio frequency treatment of the tissue. Alternatively, needles 183 may be omitted and needleless radio frequency waves or ultrasound beams may be used to treat incontinence, as described hereinabove.

After the preferred treatment is completed, basket 172 is returned to the contracted configuration by retracting rod 176 proximally with respect to elongated shaft 181 to cause struts 171 to be contained within central lumen 177.

Figure 9:
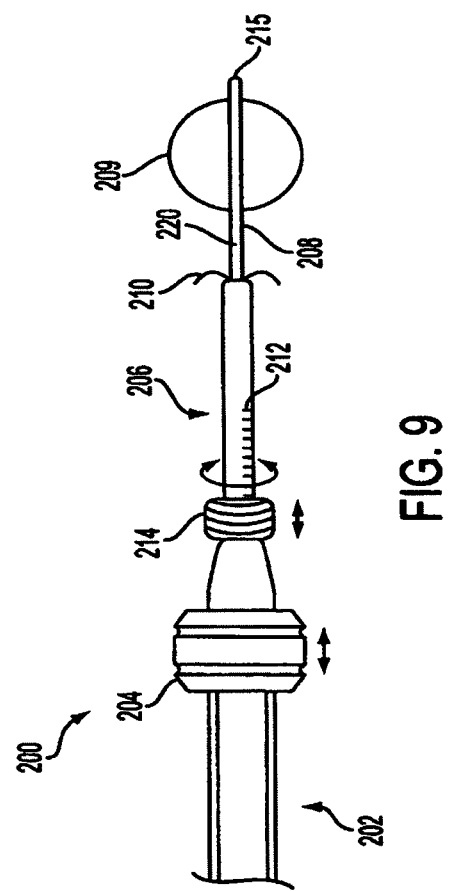
FIG. 9 is a side view of a device that allows movement of a means for treating with respect to an expandable member.

Referring now to FIGS. 9-10, apparatus and methods for longitudinally advancing the spacing between the tissue treating elements and the expandable member are described. In FIG. 9, apparatus 200 is provided in accordance with apparatus 20 of FIG. 1, except as noted below. Apparatus 200 comprises handle 202 and knob 204, which are similar in structure to handle 31 and knob 57 of FIG. 1, respectively.

Apparatus 200 further comprises elongated shaft 206 having proximal and distal ends and actuator 214 disposed about the proximal end. Measurement indicia 212 preferably are provided on a lateral surface of elongated shaft 206. Illustratively, needle electrodes 210 are shown for providing energy to the submucosal layer of the urethral wall, although it will be apparent that needleless electrodes, an ultrasound transducer or cryogenic probe, as described hereinabove, may be substituted for needle electrodes 210.

Apparatus 200 further comprises shaft 208 having proximal and distal ends and expandable member 209 disposed on the distal end. Shaft 208 preferably is affixed to an interior surface of handle 202 and may include inflation lumen 220 extending between the proximal and distal ends that communicates with expandable member 209.

Figure 10A:
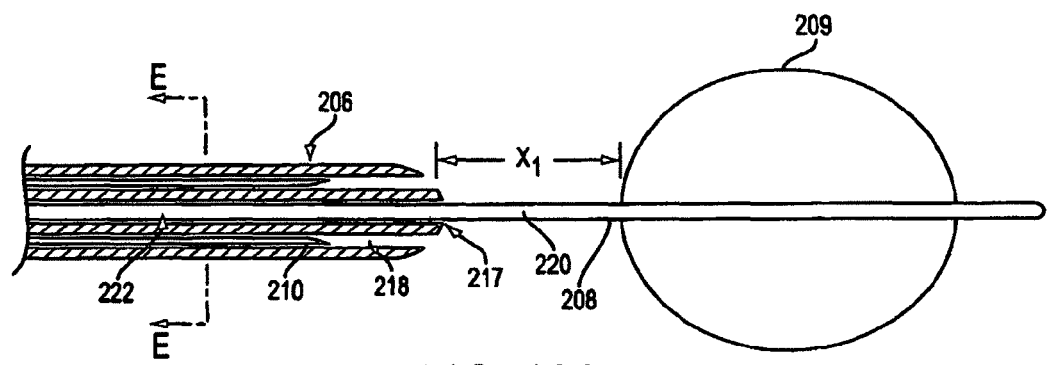
FIGS. 10A-10D are, respectively, a side sectional view of apparatus of FIG. 9 in a first position, cross-sectional views along line E-E of FIG. 10A illustrating two alternative configurations, and a side sectional view of apparatus of FIG. 9 in a second position.

Referring now to FIG. 10A, a side sectional view of the distal end of apparatus 200 is provided. Elongated shaft 206 preferably comprises central lumen 217 having an inner diameter slightly larger than an outer diameter of expandable member shaft 208. Inflation lumen 220 is in fluid communication with expandable member 209, while lumens 218 house needle electrodes 210 in the contracted state (see FIG. 10A).

Figure 10B:
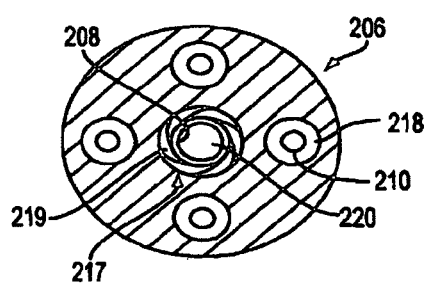

Region 222 of shaft 208 may be threaded to provide threaded interface 219 between shaft 208 and central lumen 217 of elongated shaft 206, as shown in FIG. 10B. Threaded interface 219 provides for controlled longitudinal movement of elongated shaft 206 with respect to shaft 208 when actuator 214 of FIG. 9 is rotated circumferentially.

Figure 10C:
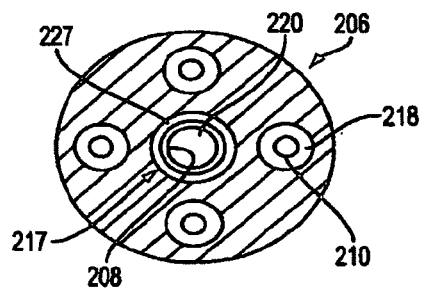
Figure 10D:
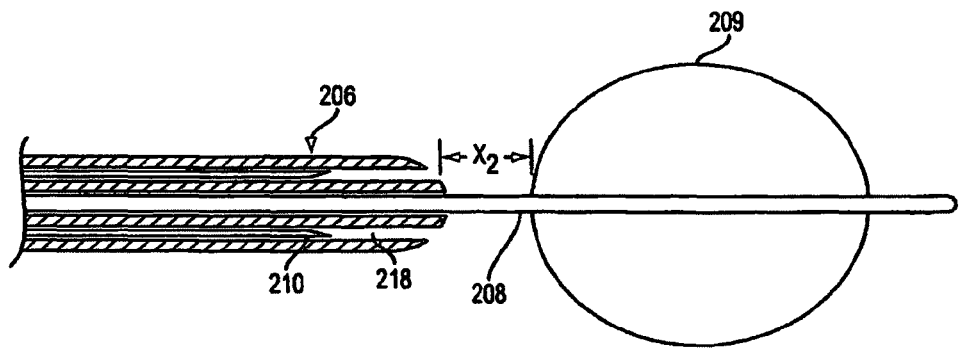

Referring to FIG. 10C, the threaded interface between elongated shaft 206 and shaft 208 is omitted and small gap 227 is provided between central lumen 217 and shaft 208. Gap 227 allows for straight translation of elongated shaft 206 with respect to shaft 208 when actuator 214 is longitudinally advanced and handle 202 is held stationary.

Using the technique of FIGS. 9-10, a physician may perform a first treatment at a distance of about $x_1$ from the bladder outlet, as shown in FIG. 10A, assuming that expandable member 209 is disposed within the bladder and then retracted against the bladder outlet. The physician then may perform a second treatment at a distance of about $x_2$ from the bladder outlet by actuator 214 as described hereinabove. Measurement indicia 212 may be used as a distance guide when a physician manipulates the distance between $x_1$ and $x_2$ using actuation handle 214.

Figure 11:
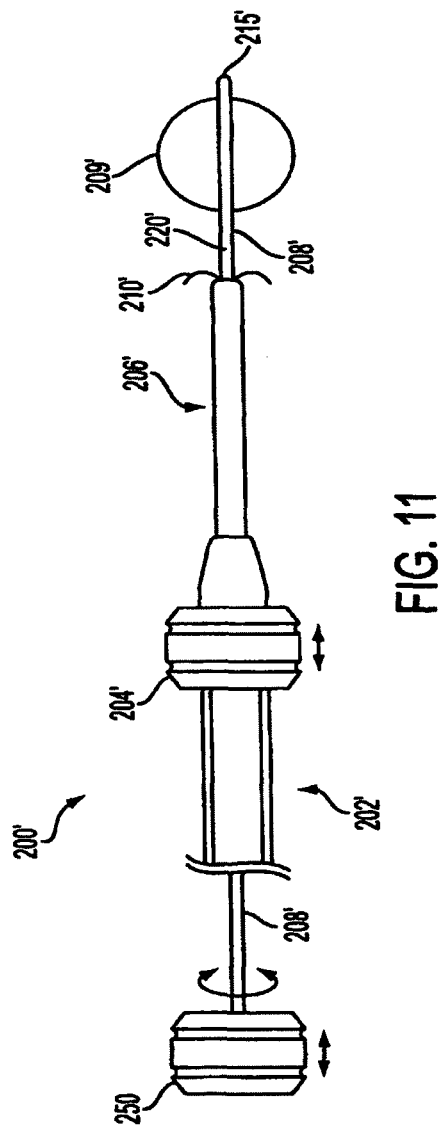
FIG. 11 is a side view of a device that allows movement of an expandable member with respect to a means for treating.

Referring now to FIG. 11, an alternative embodiment of apparatus configured to longitudinally advance the spacing between the tissue treating elements and the expandable member is described. In FIG. 11, apparatus 200' is provided substantially in accordance with apparatus 200 of FIGS. 9-10, except as noted below.

In the embodiment of FIG. 11, shaft 208' extends through elongated shaft 206' and preferably is coupled to actuator 250 instead of being affixed to an interior surface of handle 202', as described in the embodiment of FIGS. 9-10. Actuator 250 may be disposed about handle 202' in a manner similar to the manner in which knob 57 of FIG. 1 is disposed about handle 31, as described hereinabove. Alternatively, actuator 250 may be disposed proximal of handle 202'. For example, shaft 208' may extend through handle 202', through an aperture or port (not shown) disposed at the proximal end of handle 202', and then may be coupled to actuator 250 proximal of the handle.

Apparatus 200' may comprise a threaded interface between shaft 208' and a central lumen of elongated shaft 206', as described in FIG. 10B hereinabove. The threaded interface provides for controlled longitudinal movement of shaft 208' with respect to elongated shaft 206' when actuator 250 is rotated circumferentially and handle 202' is held stationary.

Alternatively, a small gap, such as described hereinabove with respect to FIG. 10C, may be provided between the central lumen of elongated shaft 206' and shaft 208'. This permits straight translation of shaft 208' with respect to elongated shaft 206' when actuator 250 is advanced or retracted and handle 202' is held stationary. Measurement indicia (not shown) may be disposed on handle 202' or shaft 208' to determine the spacing between tissue treating elements 210' and expandable member 209'.

Handle 202' also may comprise a central lumen, e.g., as described hereinabove with respect to FIGS. 10B-10C, that guides shaft 208' through handle 202'. The central lumen of handle 202' may be used alone or in conjunction with the central lumen of elongated shaft 206' to serve as a guide for shaft 208' along the length of the device.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus for remodeling at least one treatment site within the lower urinary tract of a female patient, the lower urinary tract including a urethra having a urethral lumen and a bladder having a bladder outlet, the apparatus comprising:
   an elongated shaft having proximal and distal ends and a distal region disposed adjacent to the distal end;
   markings on the shaft configured to indicate depth of insertion;
   a handle coupled to the proximal end;
   a plurality of needle electrodes extendable from around the shaft in a plane and configured to emit energy to treat a submucosal layer of the urethra or bladder outlet to cause a reduction in the compliance of the submucosal layer; and
   an expandable member deployable at a predetermined distance distal of the plurality of needle electrodes, the expandable member adapted to be deployed in the bladder.

2. The apparatus of claim 1 wherein the anchoring member comprises a balloon that is affixed to the distal region of the elongated shaft.

3. The apparatus of claim 1 wherein the anchoring member comprises a self-expandable basket.

4. The apparatus of claim 3 wherein the self-expandable basket comprises a plurality of flexible struts coupled to a rod, wherein the rod is disposed within a central lumen of the elongated shaft.

5. The apparatus of claim 4 wherein the self-expandable basket comprises a contracted state in which the plurality of flexible struts are constrained within the central lumen of the elongated shaft and a deployed state in which the plurality of flexible struts assume a predetermined curvature extending radially outward from the elongated shaft.

6. The apparatus of claim 5 wherein the plurality of flexible struts comprise a shape-memory material.

7. The apparatus of claim 1 further wherein the at least one irrigation port is disposed in a lateral surface of the elongated shaft and configured to provide irrigation fluid over from the shaft.

8. A method for remodeling at least one treatment site within the lower urinary tract of a female patient, the lower urinary tract including a urethra having a urethral lumen and a bladder having a bladder outlet, the method comprising:
   inserting a distal end of a device though the urethra thought the bladder neck outlet and into the urethra, the device having an elongate shaft with proximal and distal ends and markings on the shaft to indicate depth of insertion, a handle coupled to the proximal end, an expandable member disposed near the distal end, and a plurality of needle electrodes disposed a predetermined distance proximally of the expandable member;
   reading a first depth measurement from the markings on the shaft;
   extending the plurality of needle electrodes from a retracted position within the shaft to an extended position to advance the needle electrodes into tissue surrounding the urethra at a treatment site to form a first plane relative to the treatment site;

supplying radio frequency energy to the plurality of needle electrodes for a predetermined time to remodel tissue surrounding the urethra at the treatment site;

retracting the plurality of needles into the shaft;

rotating the shaft within the urethra;

positioning the shaft at the same first depth measurement; and extending the plurality of needle electrodes from the retracted position within the shaft to the extended position to advance the needle electrodes into tissue surrounding the urethra at a treatment site in the same plane as the first plane.

9. The method of claim 8, further comprising supplying radio frequency energy to the plurality of needle electrodes for a predetermined time to remodel tissue after extending the plurality of needle electrodes from the retracted position within the shaft to the extended position to advance the needle electrodes into tissue surrounding the urethra at a treatment site in the same plane as the first plane.

10. The method of claim 8 further comprising: providing a flow of cooling liquid in the urinary tract to cool the urethra in the treatment site.

11. The method of claim 8 further comprising sensing the impedance of tissue in the vicinity of the plurality of needle electrodes.

12. The method of claim 8 further comprising sensing the temperature of the plurality of needle electrodes to ascertain whether a predetermined temperature is being exceeded; and terminating the supply of radio frequency energy to the plurality of needle electrodes when the predetermined temperature for that needle electrode is exceeded.

13. The method of claim 8 further comprising sensing the temperature of tissue in the vicinity of each one of the plurality of needle electrodes; and terminating the supply of radio frequency energy to each one of the plurality of needle electrodes when the temperature of the tissue in the vicinity of that electrode exceeds a predetermined temperature.

* * * * *